US005797886A

United States Patent [19]
Roth et al.

[11] Patent Number: 5,797,886
[45] Date of Patent: *Aug. 25, 1998

[54] CATHETER APPARATUS WITH MEANS FOR SUBCUTANEOUS DELIVERY OF ANESTHETIC AGENT OR OTHER FLUID MEDICAMENT

[75] Inventors: Robert Roth, Festus, Mo.; Fred P. Lampropoulos, Sandy, Utah; Jim Mottola, South Jordan, Utah; Arlin Dale Nelson, Midvale, Utah; Jerrold L. Foote, Salt Lake City, Utah

[73] Assignee: Merit Medical Systems, Inc., South Jordan, Utah

[*] Notice: The term of this patent shall not extend beyond the expiration date of Pat. No. 5,405,334.

[21] Appl. No.: 622,458

[22] Filed: Mar. 22, 1996

Related U.S. Application Data

[63] Continuation-in-part of Ser. No. 417,824, Apr. 6, 1995, Pat. No. 5,533,986, which is a continuation-in-part of Ser. No. 198,625, Feb. 18, 1994, Pat. No. 5,405,334.

[51] Int. Cl.⁶ .................................................. A61M 5/00
[52] U.S. Cl. .................................................. 604/264
[58] Field of Search .......................... 604/153, 164, 604/264, 280–284, 53

[56] References Cited

U.S. PATENT DOCUMENTS

| | | | |
|---|---|---|---|
| 1,968,997 | 8/1934 | Drucker | 604/164 |
| 3,670,729 | 6/1972 | Bennett et al. | 604/164 |
| 4,149,535 | 4/1979 | Volder | 604/164 |
| 4,306,562 | 12/1981 | Osborne | 128/348 |
| 4,391,029 | 7/1983 | Czuba et al. | 29/450 |
| 4,581,019 | 4/1986 | Curelaru et al. | 604/164 |
| 4,865,593 | 9/1989 | Ogawa et al. | 604/264 |
| 5,125,904 | 6/1992 | Lee | 604/164 |
| 5,147,334 | 9/1992 | Moss | 604/264 |
| 5,158,553 | 10/1992 | Berry et al. | 604/248 |
| 5,178,611 | 1/1993 | Rosenberg | 604/172 |
| 5,207,655 | 5/1993 | Sheridan | 604/247 |
| 5,250,038 | 10/1993 | Melker et al. | 604/264 |
| 5,254,104 | 10/1993 | Furlow et al. | 604/264 |
| 5,267,966 | 12/1993 | Paul | 604/167 |
| 5,269,755 | 12/1993 | Bodicky | 604/53 |
| 5,282,785 | 2/1994 | Shapland et al. | 604/21 |
| 5,300,032 | 4/1994 | Hibbs et al. | 604/164 |
| 5,324,276 | 6/1994 | Rosenberg | 604/269 |
| 5,330,449 | 7/1994 | Prichard et al. | 604/282 |
| 5,354,271 | 10/1994 | Voda | 604/49 |
| 5,405,334 | 4/1995 | Roth et al. | 604/264 |

OTHER PUBLICATIONS

Lambert et al., *New Vascular Sheath for Subcutaneous Drug Administration: Design, Animal Testing, and Clinical Application for Pain Prevention after Angioplasty*, Catheterization and Cardiovascular Diagnosis 37, pp. 68–72 (1996).

*Primary Examiner*—Manuel Mendez
*Attorney, Agent, or Firm*—Workman Nydegger Seeley

[57] ABSTRACT

A novel catheter apparatus for use in delivering an anesthetic agent or other fluid medicament to the portion of subcutaneous tissue through which a catheter device has been inserted into a patient, thereby allowing the catheter device to be retracted without causing pain or discomfort to the patient. The catheter device has an indwelling cannula adapted for insertion through subcutaneous tissue into a patient's body. A sheath is selectively disposed about the cannula so as to be positioned within the subcutaneous tissue once the cannula has been inserted into the body. The sheath may include a plurality of longitudinal bores which act as a lumen to provide fluid medicament to delivery holes on the outside of the sheath. The delivery holes permit the anesthetic agent or fluid medicament to be delivered to the subcutaneous tissue. A light permeable hub means may be used to maintain a fluid tight connection between the sheath means and a storage container for anesthetic agent or fluid medicament.

21 Claims, 19 Drawing Sheets

CATHETER APPARATUS WITH MEANS FOR SUBCUTANEOUS DELIVERY OF ANESTHETIC AGENT OR OTHER FLUID MEDICAMENT

RELATED APPLICATION INFORMATION

This application is a continuation-in-part of U.S. application Ser. No. 08/417,824, filed on Apr. 6, 1995 now U.S. Pat. No. 5,533,986 which is a continuation-in-part of U.S. application Ser. No. 08/198,625, filed on Feb. 18, 1994, now U.S. Pat. No. 5,405,334 both of which are incorporated herein by reference.

BACKGROUND OF THE INVENTION

1. The Field of the Invention

This invention relates to a catheter apparatus with a means for subcutaneous delivery of anesthetic agents or other fluid medicaments. More particularly, this invention relates to a catheter apparatus having subcutaneous infusion ports that provide for the administration of a local anesthesia or other medicaments to an area of subcutaneous tissue through which a cannula has been inserted.

2. The Present State of the Art

Catheter devices are widely used for a variety of medical applications. Generally, a catheter is a hollow, tubular cannula that is capable of being inserted into canals, vessels, passageways, or other body cavities so as to permit injection or withdrawal of fluids, or to keep a passage open. Other catheter devices are used for controlling, directing and placing medical devices, such as intubation tubes or dilation catheters, into a body cavity, such as the trachea, a blood vessel, or the heart. These types of insertion catheters are commonly referred to as intubators, insertion sheaths, and/or dilators. Given that catheters are used for such a wide variety of applications, catheters are implemented in a variety of designs, shapes and sizes. However, when used, almost all catheters share the universal characteristic of having to be passed through the skin and subcutaneous tissue of the patient so as to be inserted into the proper body cavity.

Depending on the medical procedure, the catheter is very often left in the body cavity over a relatively long period of time. As such, the skin and subcutaneous tissue through which the catheter device is inserted often becomes very swollen and tender, and thus extremely sensitive. Consequently, when the catheter is eventually retracted from the patient, the patient will often experience great discomfort. This discomfort may agitate the patient and thereby hinder the ability of medical personnel to effectively retract the catheter and/or treat the patient.

For example, in a percutaneous transluminal coronary angioplasty (PTCA) procedure, a patient is administered a local anesthesia and an intravascular sheath introducer (a type of catheter device) is inserted through the patient's skin in the groin area and into the femoral artery. In so doing, the sheath introducer necessarily passes through the area of subcutaneous tissue that lies between the skin and the femoral artery. Once inserted, the sheath introducer catheter provides a means for introducing the dilation catheter for performing the PTCA procedure.

Following the PTCA procedure, the sheath introducer is usually left within the femoral artery for a period ranging between four to twenty-four hours. Typically, the sheath is left in place because blood thinning drugs, such as Heparin, are administered to the patient. The effects of such drugs must wear off before the sheath can be removed in order to avoid hemorrhaging problems. Similarly, the device may be left in the patient as a precaution, in case quick access to the femoral artery is needed due to subsequent complications, such as an abrupt closure of the artery. In any event, by the time the sheath is retracted, the patient's skin and subcutaneous tissue through which the catheter is inserted is typically very swollen, bruised and tender. Also, by this time, the numbing effects of the earlier administered local anesthesia have completely worn off. Consequently, as the sheath is retracted from the femoral artery, the subcutaneous tissue and the overlying skin, the patient can experience considerable pain.

Pain experienced during sheath removal is known to occasionally cause vasovagal syncope type reactions, which can potentially result in a variety of undesirable patient responses—including a drop in blood pressure and heart rate. This can be hazardous when it occurs so soon after the PTCA procedure, and may thus require treatment with intravenous Atropine, or other drugs. Pain may also cause the patient to become agitated, which makes it difficult for medical personnel to properly administer arterial compression. This can lead to a hematoma formation within the subcutaneous tissue adjacent to the catheter.

Although medical personnel can administer a local anesthesia to the area, this must be done with a hypodermic needle, which usually causes as much discomfort or pain as the actual retraction of the catheter device. Thus, there is not a medical device available which adequately relieves a patient's discomfort during catheter retraction, and there is a need to be able to administer a local anesthesia to the subcutaneous tissue surrounding a catheter device prior to the retraction of the device, in a relatively painless and easy manner.

A challenging aspect of the assembly of a catheter apparatus employed to administer local anesthesia is the assembly of a hub for connecting a line for supplying anesthesia from an anesthesia storage chamber to the means for subcutaneous delivery of the anesthesia. To provide for a fluid connection between the anesthesia storage chamber and the means for subcutaneous delivery, it is desirable to employ a hub linking the line from the storage chamber to the means for subcutaneous delivery. However, to properly connect the anesthesia supply line to the means for subcutaneous delivery, a fluid tight seal must be maintained throughout the path between the storage chamber and the means for subcutaneous delivery. Methods previously employed for creating a fluid tight seal, such as a hot insert molding process may melt the delicate materials used to form the means for subcutaneous delivery.

In addition, because of the fluid pressures within the means for subcutaneous delivery, it would be advantageous within the art to attach the delivery means to the hub in a manner that reinforces the delivery means and prevents it from deforming. In addition, although a fluid tight seal and reinforcing features are desirable, it is also desirable to achieve these qualities with a quick-cure adhesive to reduce manufacturing costs. Thus, there is a need within the art to be able to assemble a fluid tight, strong hub which can be quickly assembled without damaging the means for subcutaneous delivery and which reinforces the delivery means against deformation.

SUMMARY AND OBJECTS OF THE INVENTION

The apparatus of the present invention has been developed in response to the present state of the art, and in particular, in response to the problems involved with the pain and discomfort that is experienced by a patient when a catheter device is removed. Thus, it is an overall object of the present invention to provide an apparatus which provides for the ability to painlessly administer local anesthesia or other medicaments to an area of subcutaneous tissue through which a catheter device has been inserted.

A further object of the present invention is to provide an apparatus that permits subcutaneous delivery of such medicaments but which also prevents bodily fluids from entering the apparatus while it is inserted and remains within the patient's body.

Yet another important object of the present invention is to provide an anesthetizing catheter sheath apparatus that can be manufactured either as an integral part of a catheter device, or as an apparatus that can be detachably mounted to a catheter device.

An additional object of this invention is to provide a light-permeable hub means which can be assembled using ultraviolet rays, natural light or other radiation in order to accurately dispose and cure a quick-cure adhesive within the hub means, and thereby create a fluid tight seal within the hub means without damaging the structure of the anesthetizing catheter sheath apparatus.

An additional object of the invention is to provide a sheath means having an interior lumen comprised of a series of longitudinal bores which assist in the delivery of fluid medicament.

An additional object is to provide a means for regulating the position of the sheath means within the body.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

Briefly summarized, the foregoing and other objects are achieved with a catheter apparatus that is inserted into a patient's body through subcutaneous tissue. In one embodiment, a sheath fits over the catheter and is designed for insertion together with the catheter through the subcutaneous tissue. Once the catheter device is inserted into the patient's body, the outer surface of the catheter device necessarily passes through the patient's skin and a portion of underlying, subcutaneous tissue. The sheath which is disposed on the outer surface of the catheter device is also thus inserted through the subcutaneous tissue. Prior to retracting the catheter device, medical personnel can administer an anesthetic agent by infusing it into the surrounding subcutaneous tissue from the anesthetizing sheath. In this way, the subcutaneous tissue will be numbed, and the patient will experience no pain while the catheter device is retracted. In addition to anesthetic agents, the sheath can also be used to deliver a wide variety of other types of fluid medicaments to the subcutaneous tissue. For instance, the sheath may be used to deliver topical antibacterial agents to the tissue.

In one embodiment of the present invention, the anesthetizing sheath apparatus can be permanently mounted to the catheter device, and is thus manufactured as an integral part of the catheter device.

In another embodiment of the present invention, the anesthetizing sheath can be detachably mountable to the outer surface of the catheter device. In this manner, the anesthetizing sheath can be designed for use with any of a wide variety of existing catheter devices already on the market, thereby increasing its versatility.

In a still further embodiment of the invention, the anesthetizing sheath includes a primary lumen for passage of a cannula and one or more smaller, interior lumens radially disposed about the primary lumen, into which the anesthetic agent is injected and from which the anesthetic agent is infused into surrounding subcutaneous tissue.

In a still further embodiment of the present invention, a hub for the delivery of fluid medicament to the anesthetizing sheath includes a multi-component transparent or translucent hub. The assembly of the components to form the hub retains the anesthetizing sheath in a desirable, predetermined position by interposing the sheath between a proximal hub component and a distal hub component.

After the anesthetizing sheath is disposed between the components, and after adhesive is allowed to wick into the concentric raceways thereby created, ultra-violet or visible light radiation may be emitted onto the hub assembly such that the adhesive within the raceways cures, bonding the anesthetizing sheath and components together. By employing a light permeable hub, it is possible to place radiation-activated adhesive, such as ultraviolet curable adhesive in the proper location within the hub, then quickly cure the accurately placed adhesive with a source of radiation, such as ultraviolet rays, natural light, or some other form of radiation.

The source of radiation, while creating a fluid tight seal as a result of the cured adhesive, does not damage the components of the hub or the anesthetizing sheath, whereas other procedures, such as insert molding, could melt or otherwise deform the anesthetizing sheath, particularly when delicate, individual bores are used in the lumen structure.

These and other objects, features, and advantages of the present invention will become more fully apparent from the following description and appended claims, or may be learned by the practice of the invention as set forth hereinafter.

BRIEF DESCRIPTION OF THE DRAWINGS

In order to more fully understand the manner in which the above-recited and other advantages and objects of the invention are obtained, a more particular description of the invention will be rendered by reference to specific embodiments thereof which are illustrated in the appended drawings. Understanding that these drawings depict only typical embodiments of the invention and are therefore not to be considered limiting of its scope, the invention in its presently understood best mode for making and using the same will be described with additional specificity and detail through the use of the accompanying drawings as listed hereinafter.

DETAILED DESCRIPTION OF THE PREFERRED EMBODIMENTS

Figure 1:
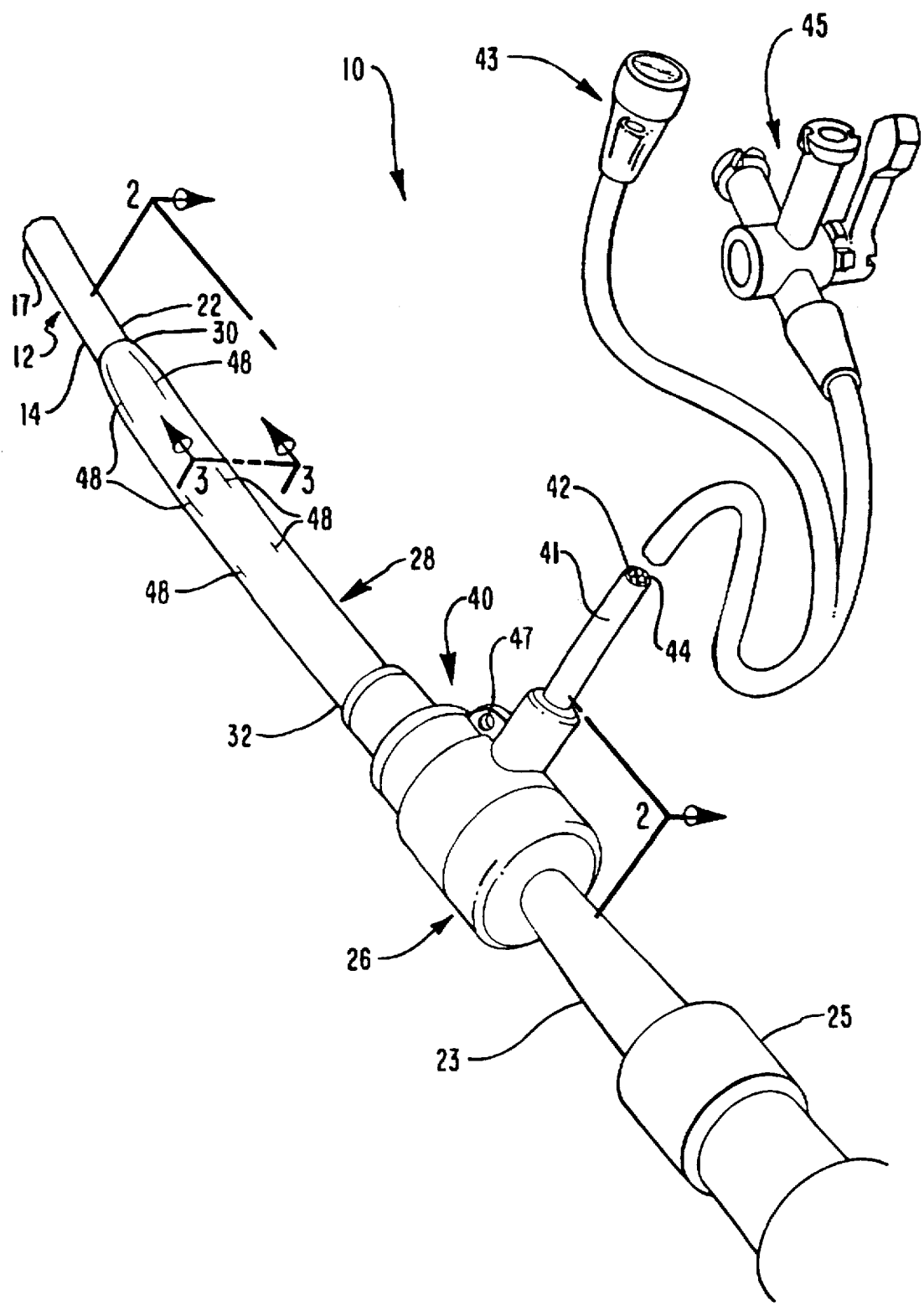
FIG. 1 is a perspective view illustrating one embodiment of the catheter apparatus of the present invention.

Reference is next made to the drawings, wherein like parts are designated with like numerals throughout. Referring first to FIG. 1, one embodiment of the invention is illustrated. FIG. 1 represents a perspective view of the catheter apparatus of the present invention, designated generally at 10. Catheter apparatus 10 includes a catheter means as for example a catheter device designated generally at 12, for insertion through subcutaneous tissue. As used herein, the term catheter device is intended to broadly cover the general category of cannula-type devices referred to as catheters. Thus the term catheter device is intended to refer to any hollow, tubular cannula-type device that is capable of being inserted into canals, vessels, passageways, or other body cavities so as to permit injection or withdrawal of fluids, or to keep a passage open. Further, the term is intended to include insertion devices which are used for controlling, directing and placing medical devices, such as intubation tubes or dilation catheters, into a body cavity, such as the trachea, a blood vessel, or the heart, and which are commonly referred to as intubators, insertion sheaths, and/or dilators.

For purposes of example, the catheter device 12 illustrated in FIG. 1 is an insertion sheath comprised of an indwelling cannula 14 which is adapted for insertion through subcutaneous tissue and into a patient's body. As is better shown in FIG. 2, the cannula 14 is inserted into a patient's body (typically via a guide wire while the patient is numbed with a local anesthetic) so as to have a distal end 17 disposed within a body cavity, such as a blood vessel 16. As is shown, the cannula 14 necessarily passes through the patient's skin layer 18 and the area of subcutaneous tissue 20 that lies between the skin layer 18 and the body cavity, such as the blood vessel 16. Thus, once the cannula 14 is properly positioned, a portion 22 of the cannula 14 remains disposed within the area of subcutaneous tissue 20.

Once in place, the insertion sheath cannula 14 is used for controlling and directing the placement of another medical device, as for example a dilation catheter 24 for use in a PTCA procedure. The dilation catheter 24 is inserted into the hollow cannula 14 via the proximal hub end 26 of the catheter device 12, and the tubing 23 and connector 25 attached thereto. The proximal hub end 26 remains positioned outside of the body. Upon completion of the PTCA (or related) procedure, the dilation catheter 24 is removed from the cannula 14 through the proximal hub end 26. Typically, the distal end portion 17 of the cannula 14 then remains positioned within the patient, sometimes for as long as twenty-four hours. At the end of this time period (by which time all numbing effects of the local anesthesia have worn off) the patient's skin 18 and subcutaneous tissue 20 are swollen and very sensitive, and retraction of the cannula 14 can be extremely painful.

Referring again to FIG. 1, the catheter apparatus 10 of the present invention further comprises a sheath means as for example a hollow cylindrical sleeve generally designated at 28, for placement onto at least a portion of the cannula 14 at a point intermediate of the distal end 17 and the proximal hub end 26. As is better shown in FIG. 2, the cylindrical sleeve 28 is positioned on the cannula 14 so as to be disposed on the portion 22 of cannula 14 that is surrounded by subcutaneous tissue 20 when the cannula 14 is indwelling within the patient's body.

Figure 2:
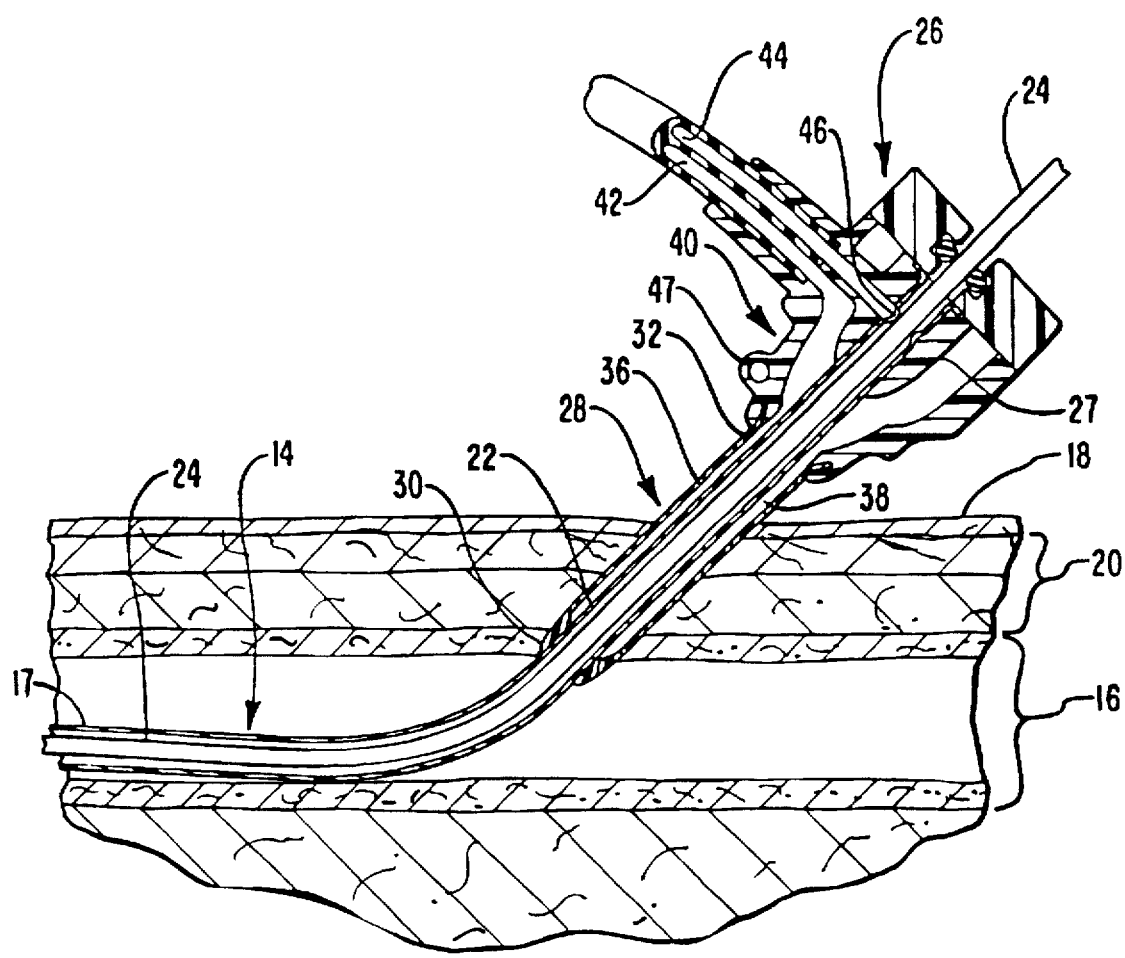
FIG. 2 is a cross-sectional view taken along line 2—2 in FIG. 1, and further illustrates the catheter apparatus of FIG. 1 disposed within a portion of a patient's body.
Figure 3:
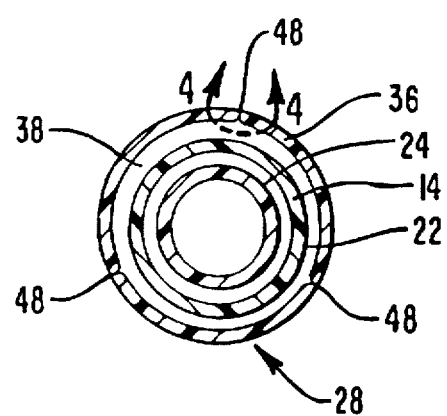
FIG. 3 is a cross-sectional view taken along line 3—3 in FIG. 1.

As is shown in the embodiment of FIGS. 1 and 2, the cylindrical sleeve 28 has a distal end 30 and a proximal end 32. The cross-sectional view of FIG. 3 illustrates how hollow cylindrical sleeve 28 has an inner diameter which is greater than the outer diameter of cannula 14, and how cylindrical sleeve 28 is positioned on cannula 14 so as to be concentric with the cannula 14. Preferably, distal end 30 of cylindrical sleeve 28 is tapered where it terminates on the outer surface of cannula 14 so that the cylindrical sleeve 28 can be inserted with little or no trauma through the outer skin layer 18 and subcutaneous tissue 20. This tapered distal end 30 is best seen in FIG. 2.

The sheath means is further comprised of a means for sealing the sheath means in a fluid tight manner around the cannula 14 so as to prevent fluids, such as blood from the body, from escaping between the cannula 14 and the sheath means. In the embodiment of FIGS. 1 and 2, for example, this sealing function is accomplished by permanently affixing the cylindrical sleeve 28 over the outer surface 22 of the cannula 14. Thus, in this embodiment, the distal end 30 of the cylindrical sleeve 28 is fused, or otherwise suitably affixed, to the cannula 14. By so doing, fluids are prevented from entering the space or interior lumen 38 between the outer surface of the cannula 14 and the cylindrical sleeve 28.

The sheath means as for example cylindrical sleeve 28, is further comprised of a means for delivering fluid medicament, such as an anesthetic agent (not shown), to essentially only that portion of subcutaneous tissue 20 that surrounds the sheath means. Delivery of fluid medicament is accomplished, for example, by way of the interior lumen 38 running from the distal end 30 to the proximal end 32 of the cylindrical sleeve 28. Delivery of fluid medicament is also aided by a hub means for delivering the fluid medicament to the interior lumen 38, and a plurality of valve means for communicating the fluid medicament from the interior lumen 38 to the subcutaneous tissue surrounding the sheath means.

By way of example, FIG. 2 illustrates cylindrical sleeve 28 as being comprised of a single cylindrical wall 36. In this particular embodiment, the interior lumen 38 is formed between the cylindrical wall 36 and the outer surface of the cannula 14. Interior lumen 38 is also shown in the cross-sectional view of FIG. 3.

By way of further example, FIGS. 1 and 2 illustrate how the hub means can be comprised of a hub 40 that is joined in a fluid tight manner to the proximal end 32 of the cylindrical sleeve 28, and to the proximal hub end 27 of the cannula 14. Hub 40 further comprises, for example, a first passageway means such as a first hub lumen 42, for communicating the fluid medicament to the interior lumen 38. In addition, hub 40 comprises a second passageway means such as second lumen 44, for providing fluid communication to the cannula 14 via a cannula access hole 46. FIG. 1 illustrates how the first and second hub lumens 42, 44 are preferably coupled to multi-lumen tube 41. Multi-lumen tube 41 is branched such that first hub lumen 42 is coupled to an infusion port 43, and second hub lumen is coupled to an I.V. valve assembly 45. In this way, a medical technician can administer fluid medicament with a syringe to the interior lumen 38 using infusion port 43.

By way of further example, FIG. 1 illustrates how the plurality of valve means are preferably comprised of a plurality of one way valve means spaced along the cylindrical sleeve 28. The one-way valve means not only allow the fluid medicament to be communicated from the interior lumen 38 to the subcutaneous tissue 20, but also act so as to prevent bodily fluids from entering the interior lumen 38. The one way valve function is provided by a plurality of one way slits 48 placed uniformly about the cylindrical sleeve 28. Because the width of the subcutaneous tissue 20 will vary from patient to patient, it is possible that the distal end 30 of the cylindrical sleeve 28, along with some of the slits 48, could be disposed within the blood vessel 16. In this situation, the one way slits 48 positioned within the portion of subcutaneous tissue 20 will properly communicate the anesthetic agent to the tissue 20, but any of the one way slits 48 that are located within the blood vessel 16 will prevent bodily fluids, such as blood, from entering the interior lumen 38.

As is further shown in FIG. 1, each slit 48 is preferably made longitudinally along the axis of the cylindrical sleeve 28. Slits 48 are uniformly located about the periphery of the cylindrical sleeve 28 so as to insure that the anesthetizing agent is evenly and uniformly delivered to the surrounding subcutaneous tissue 20. Further, the longitudinal length of each slit 48 changes depending on its location on the cylindrical sleeve 28. Preferably the slits 28 become progressively shorter as they near the proximal end 32 of the cylindrical sleeve 28. This variation in slit length is intended to help assure that fluid medicament is uniformly delivered from the proximal end 32 to the distal end 30 of sleeve 38. This may be especially important if one or more proximately located slits 48 are located outside of the patient's body during delivery of the fluid medicament.

Figure 4:
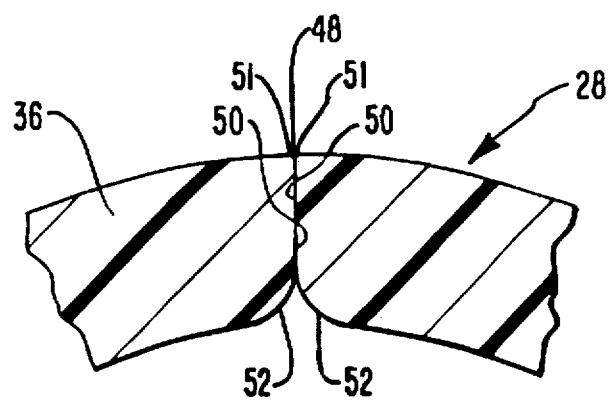
FIG. 4 is an enlarged cross-sectional view taken along line 4—4 of FIG. 3, showing a one way slit in a closed position.
Figure 5:
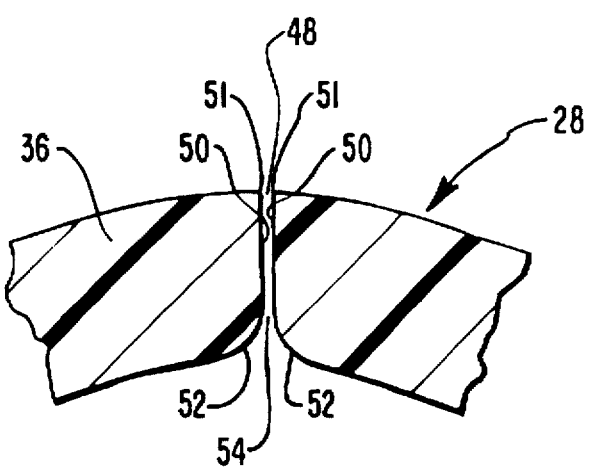
FIG. 5 is an enlarged cross-sectional view taken along line 4—4 of FIG. 3, showing a one way slit in an open position to permit infusion of anesthetic agent into surrounding subcutaneous tissue.

As is shown in FIGS. 3—5, each one way slit 48 extends completely through the cylindrical wall 36 of the cylindrical sleeve 28 so as to provide fluid communication with interior lumen 38. It is shown best in FIGS. 4 and 5 wherein each slit 48 is defined by opposed, aligned, normally abutting, parallel edges 50. FIG. 4 illustrates how a square portion 51 of the abutting edges 50 are normally engaged in a sealing relationship, and wherein the slit 48 is thereby in a closed position. The abutting edges 50 are further formed with rounded internal edge portions 52 that do not abut, but are spaced apart. In this closed position (shown in FIG. 4), the slit 48 will prevent any bodily fluids from entering the interior lumen 38.

Wall edges 50 are also capable of flexing outwardly from their closed position, responsive to a pressure generated within the interior lumen 38. In so doing, an orifice 54 is created, through which fluid such as the anesthetic agent, can flow. This open position is illustrated in FIG. 5. Thus, by applying a predetermined positive pressure to interior lumen 38, a fluid medicant such as an anesthetic agent is infused into the area of subcutaneous tissue 20 in which the cylindrical sleeve 28 is disposed, as shown in FIG. 2.

Slits 48 normally remain closed and wall edges 50 remain in an abutting position (FIG. 4). This requires that the cylindrical sleeve 28 have sufficient memory to return the slits 48 to the closed position after infusion of anesthetic agent is terminated. The cylindrical sleeve 28 may be constructed from a variety of materials with the required elasticity. Preferably, the cylindrical sleeve 28 is rigid enough to be easily inserted into the area of subcutaneous tissue 20 in conjunction with the cannula 14. At the same time, the cylindrical sleeve 28 should be flexible enough so as to conform to the movements of the patient, and such that the slits 48 exhibit the unidirectional fluid flow properties discussed above in connection with FIGS. 4 and 5.

In one embodiment, cylindrical sleeve 28 is preferably made from a nylon material. Also, Teflon, ployurethane or polyethylene materials may be suitable. The sleeve material can have a Shore A durometer in the range from about 80 to about 100 and Shore D durometer in the range of 35 to 70, and preferably will be in the range from about Shore D 40 to about 55.

It will be appreciated that the valve means may be comprised of a variety of equivalent structures. For instance, valve means could be comprised of a plurality of holes formed through the cylindrical wall 36 of the cylindrical sleeve 28. Further, this structure could provide a one way fluid flow function if the holes are made sufficiently large with respect to the width of interior lumen 38. In such an embodiment, the pressures exerted by bodily fluids, such as interstitial blood pressure, would compress the interior lumen 38 and thereby prevent back-flow of bodily fluids back into the interior lumen 38 through the holes. An illustrative example of such an embodiment is described in further detail below in connection with FIGS. 17A through 18B.

With continued reference to FIGS. 1 and 2, formed on the hub 40 near proximal end 32 of the cylindrical sleeve 28 is a suture attachment ring 47. Once the cylindrical sleeve 28, in conjunction with the insertion sheath cannula 14, has been positioned within the portion of subcutaneous tissue 20, the physician can suture, or otherwise attach, the cylindrical sleeve 28 to the patient via the suture attachment ring 47. In this manner, the cylindrical sleeve 28 will stay correctly positioned within the portion of subcutaneous tissue 20 during subsequent medical procedures, such as a PTCA. This insures that medical personnel can administer a fluid medicament, such as an anesthetic agent, to the subcutaneous tissue 20 without first having to reposition the cylindrical sleeve 28.

Figure 6:
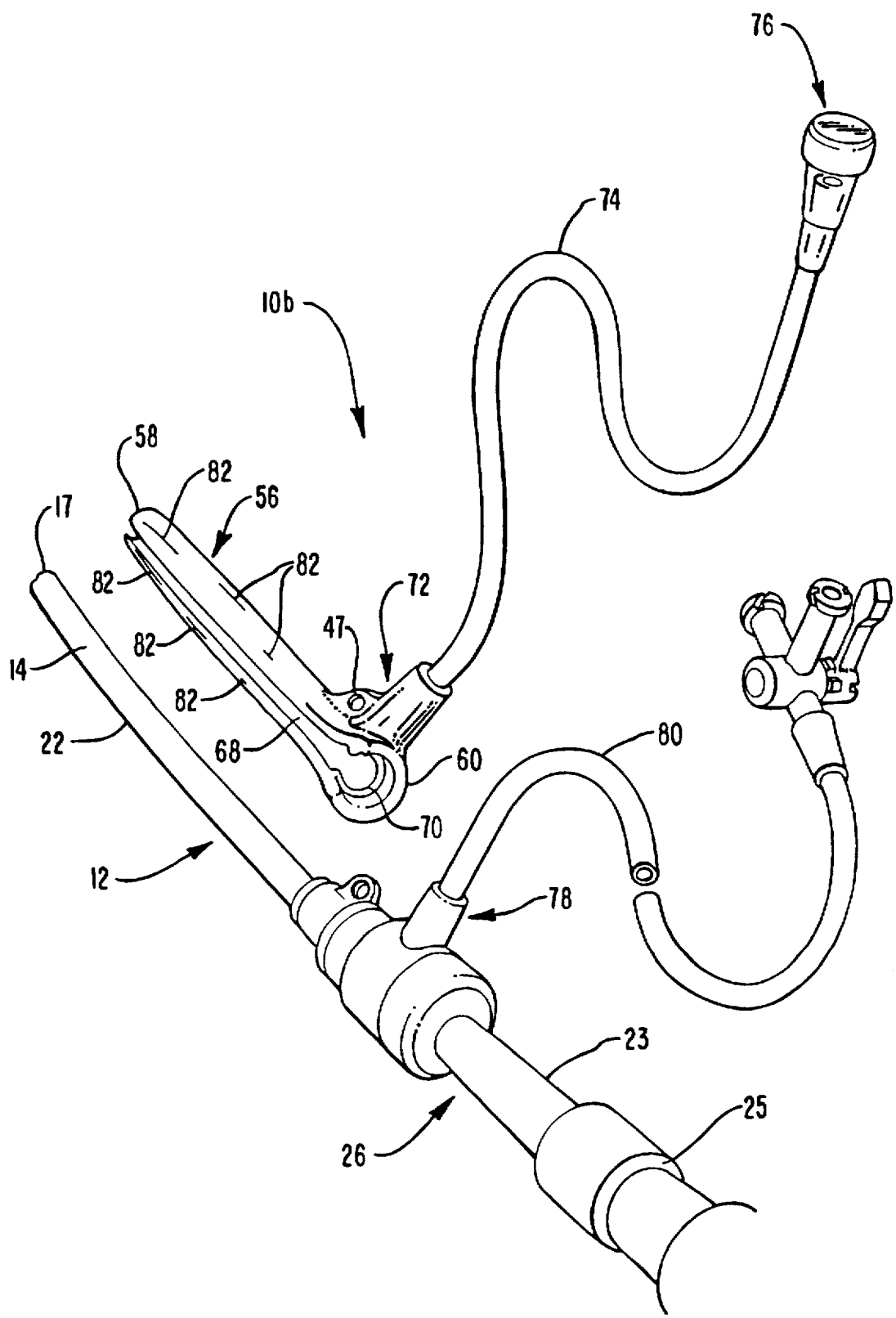
FIG. 6 is an exploded perspective view of another embodiment of the catheter apparatus of the present invention.
Figure 7:
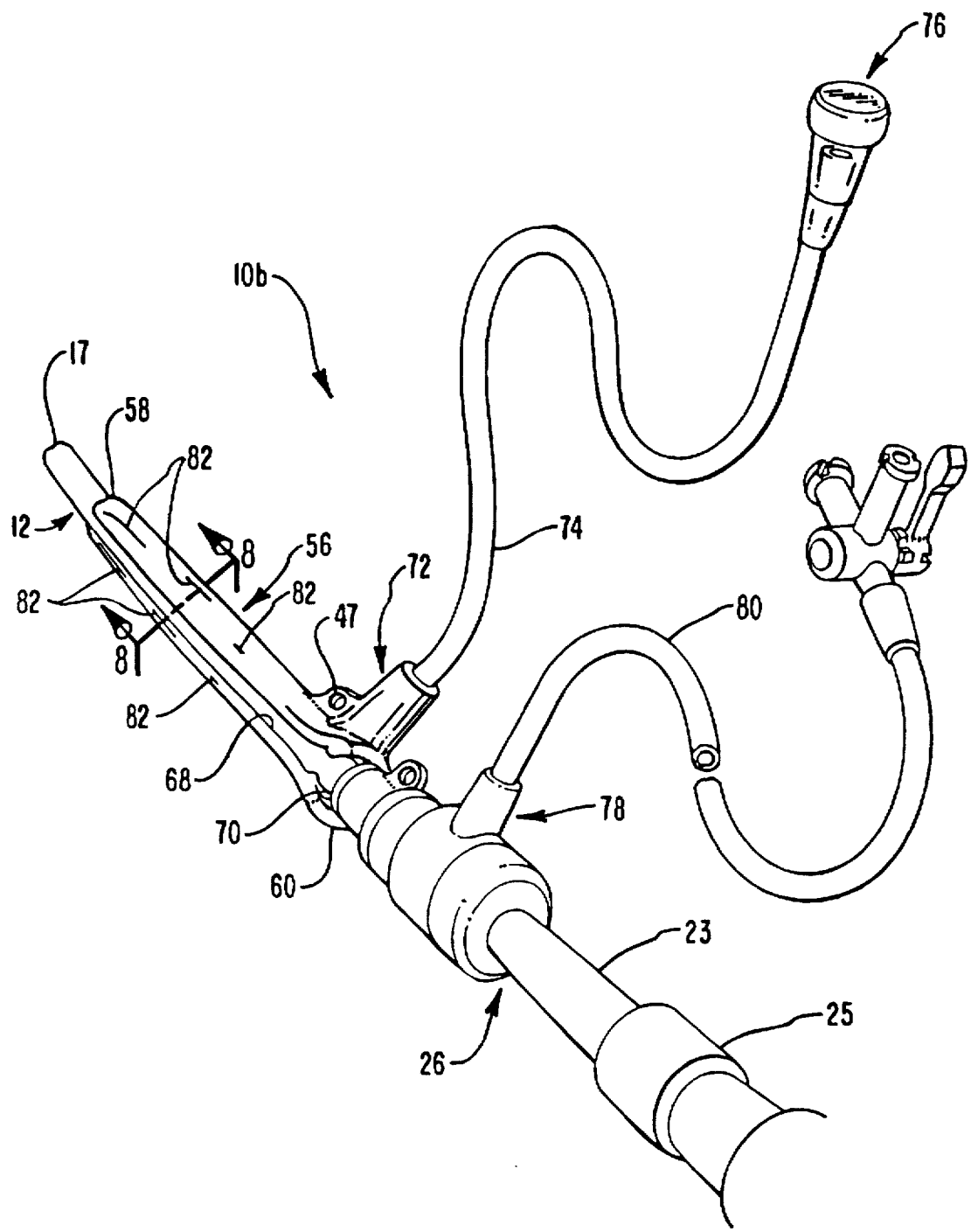
FIG. 7 is a perspective view of the anesthetizing sheath of FIG. 6 mounted to a catheter device.
Figure 8:
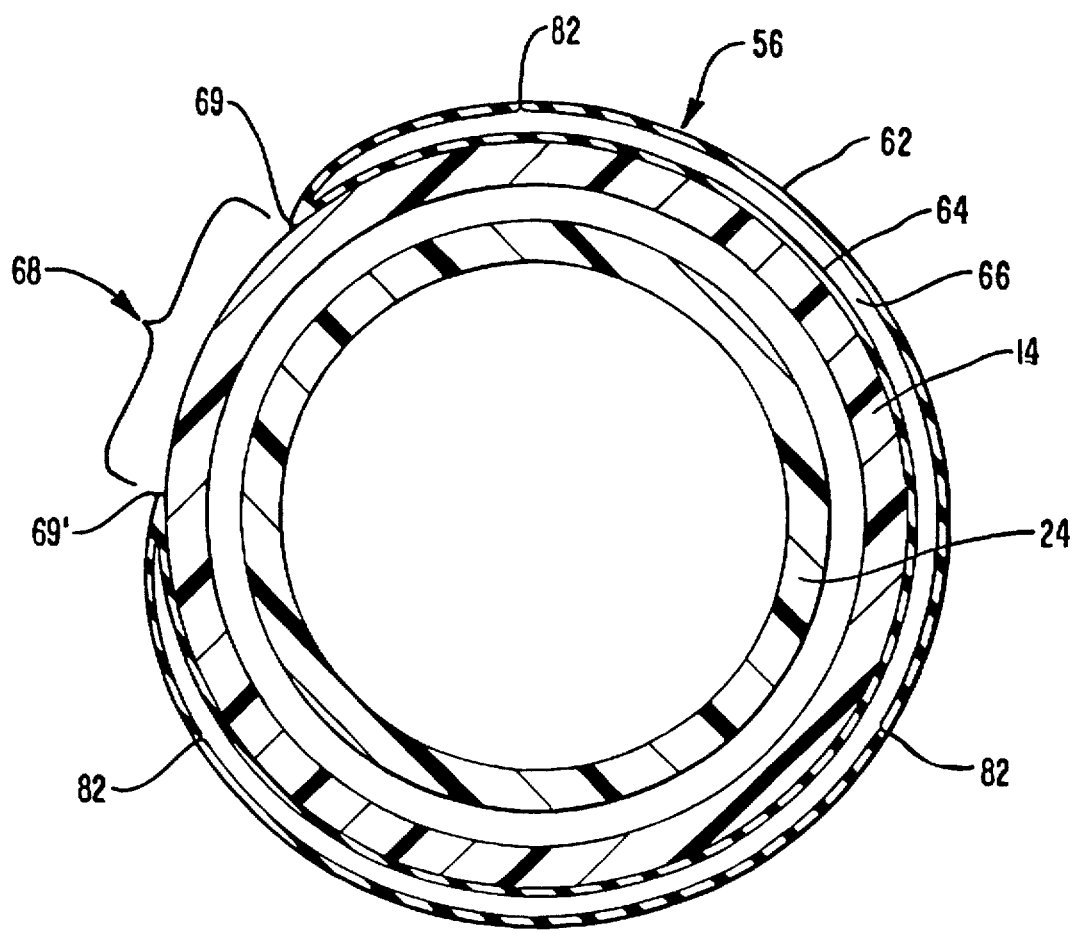
FIG. 8 is a cross-sectional view taken along line 8—8 in FIG. 7.

Another embodiment of the catheter apparatus of the present invention is illustrated in FIGS. 6 through 8, and is designated generally at 10b. Catheter apparatus 10b includes a catheter means as for example a catheter device designated generally at 12 which is essentially the same as the catheter device discussed in conjunction with FIGS. 1 through 3. That discussion will not be repeated here.

The indwelling catheter apparatus 10b also comprises a sheath means as for example a hollow cylindrical sleeve 56, for placement onto at least a portion of the cannula 14 at a point intermediate of the distal end 17 and the proximal hub end 26 of the cannula 14. However, unlike the embodiment shown in FIGS. 1 through 3, the sheath means of FIGS. 6 through 8 can be selectively attached and detached to the cannula 22, as discussed in further detail below.

As is shown in FIGS. 6 and 7, cylindrical sleeve 56 has a distal end 58 and a proximal end 60. Hollow cylindrical sleeve 56 further has an inner diameter which is greater than the outer diameter of cannula 14. This relationship is also shown in the cross-sectional view of FIG. 8. Also shown in FIG. 8 is how cylindrical sleeve 56 is positioned, in a tight fitting manner, on cannula 14 so as to be concentric with the cannula 14. Preferably, distal end 58 of cylindrical sleeve 56 is tapered with respect to the outer surface 22 of cannula 14, so that the cylindrical sleeve 56 can be inserted with little or no trauma through the portion of subcutaneous tissue 20 when it is mounted to the cannula 14.

The cylindrical sleeve 56 further comprises a means for delivering fluid medicament, such as an anesthetic agent, to the subcutaneous tissue 20 surrounding the sleeve 56. The fluid medicament delivering means comprises, for example, a means for defining an interior lumen running from the distal end 58 to the proximal end 60 of the sleeve 56, a hub means through which the fluid medicament is delivered to the interior lumen, and a plurality of one way valve means for communicating the fluid medicament from the interior lumen to the subcutaneous tissue 20 surrounding the sleeve 56 and for preventing fluids from entering the interior lumen.

By way of example, and referring now to FIG. 8, cylindrical sleeve 56 is illustrated as being comprised of a cylindrical outer wall 62 that is formed over a concentric cylindrical inner wall 64 in a spaced apart relationship. Thus, in this embodiment, an interior lumen 66 is provided by the space between the outer wall 62 and the inner wall 64.

By way of further example and with continued reference to FIGS. 6 and 7 in combination, the hub means is comprised of a first hub 72. Preferably, first hub 72 is joined in a fluid tight manner to the proximal end 60 of the cylindrical sleeve 56. First hub 72 further comprises, for example, a first passageway means such as a first hub lumen (not shown), for communicating the anesthetic agent to the interior lumen 66.

As is shown in FIGS. 6 and 7, the first hub 72 can be attached, for example, to an external tube 74 through which the anesthetic agent can be introduced to the internal lumen 66, as for example by a syringe (not shown), via an infusion port 76.

FIGS. 6 through 8 further illustrate an embodiment of the plurality of one way valve means spaced along the cylindrical sleeve 56. As is shown, each valve means is comprised of a one way slit 82 that is formed through outer wall 62 of cylindrical sleeve 56. These slits 82 are preferably substantially identical to the one way slits 48 described above in connection with FIGS. 1 through 3, and that discussion will not be repeated here.

As is further shown in FIGS. 6 through 8, in this particular embodiment sleeve 56 is further comprised of a means for selectively attaching and detaching the sleeve 56 from the cannula 14. For example, the means for selectively attaching and detaching is illustrated as being comprised of a continuous slit 68 that extends longitudinally along the entire length of the cylindrical sleeve 56. Slit 68 has a width such that the cylindrical sleeve 56 can be detachably mounted to the cannula 14 through the slit 68. The cylindrical sleeve 56 in such a mounted position is illustrated in FIGS. 7 and 8.

Referring now to FIG. 8, when cylindrical sleeve 56 is mounted to cannula 14, the cylindrical inner wall 64 is in continuous contact with the outer surface of cannula 14. This tight fitting position is maintained by the resilient properties that are preferably exhibited by cylindrical sleeve 56. As is further shown, the edges 69 and 69' where the outer wall 62 meets inner wall 64 are tapered with respect to the outer surface of the cannula 14. This permits the cylindrical sleeve 56 to be inserted with less trauma into the subcutaneous tissue, and it further forms a tight seal between the cylindrical sleeve 56 and cannula 14 so as to prevent bodily fluids from leaking between sleeve 56 and cannula 14. The sheath means of this embodiment is also comprised of a means for sealing the sheath means in a fluid tight manner around the cannula 14 so as to prevent fluids, such as blood from the body, from escaping between the cannula 14 and the sleeve 56. For example, as is shown in both FIGS. 6 and 7, this sealing is accomplished by placing an O-ring 70 between the cylindrical sleeve 56 and the outer surface of the cannula 14. Thus, when the cylindrical sleeve 56 is mounted to the cannula 14, O-ring 70 forms a fluid-tight seal, and thereby prevents any bodily fluids from leaking between sleeve 56 and cannula 14. Cylindrical sleeve 56 also has formed thereon a suture attachment ring 47, similar to the ring 47 discussed above in connection with FIGS. 1 through 3.

In the embodiment of FIGS. 6 and 7, the indwelling catheter apparatus further includes a second hub means as for example hub 78, for providing fluid communication to the cannula 14. Hub 78 is joined in a fluid tight manner to the proximal end of cannula 14. As is also shown, hub 78 can be connected to external tube 80, through which fluids may be infused to cannula 14. A dilation catheter may be introduced into cannula 14 through tubing 23 and connector 25.

Figure 9:
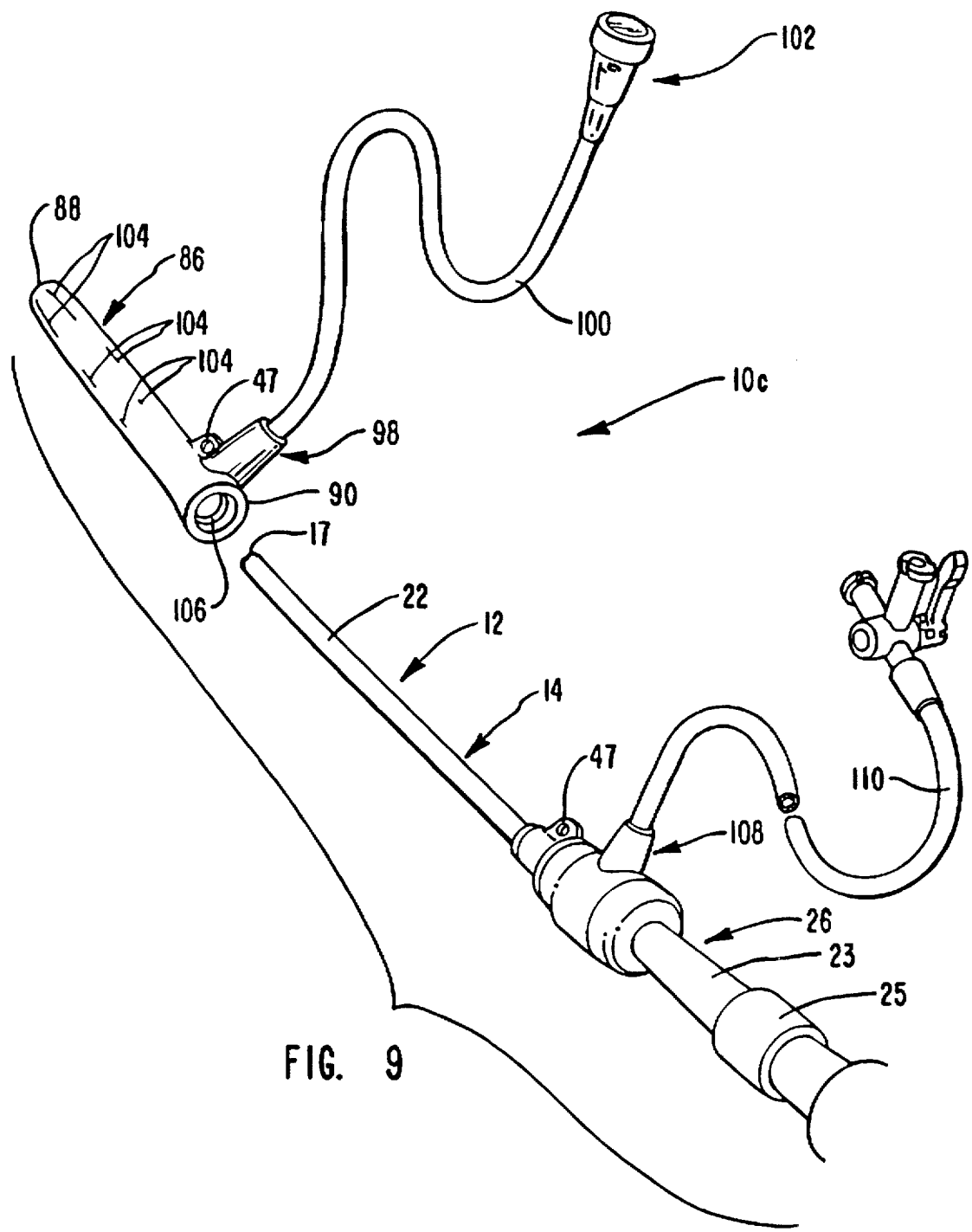
FIG. 9 is an exploded perspective view of another embodiment of the catheter apparatus.
Figure 10:
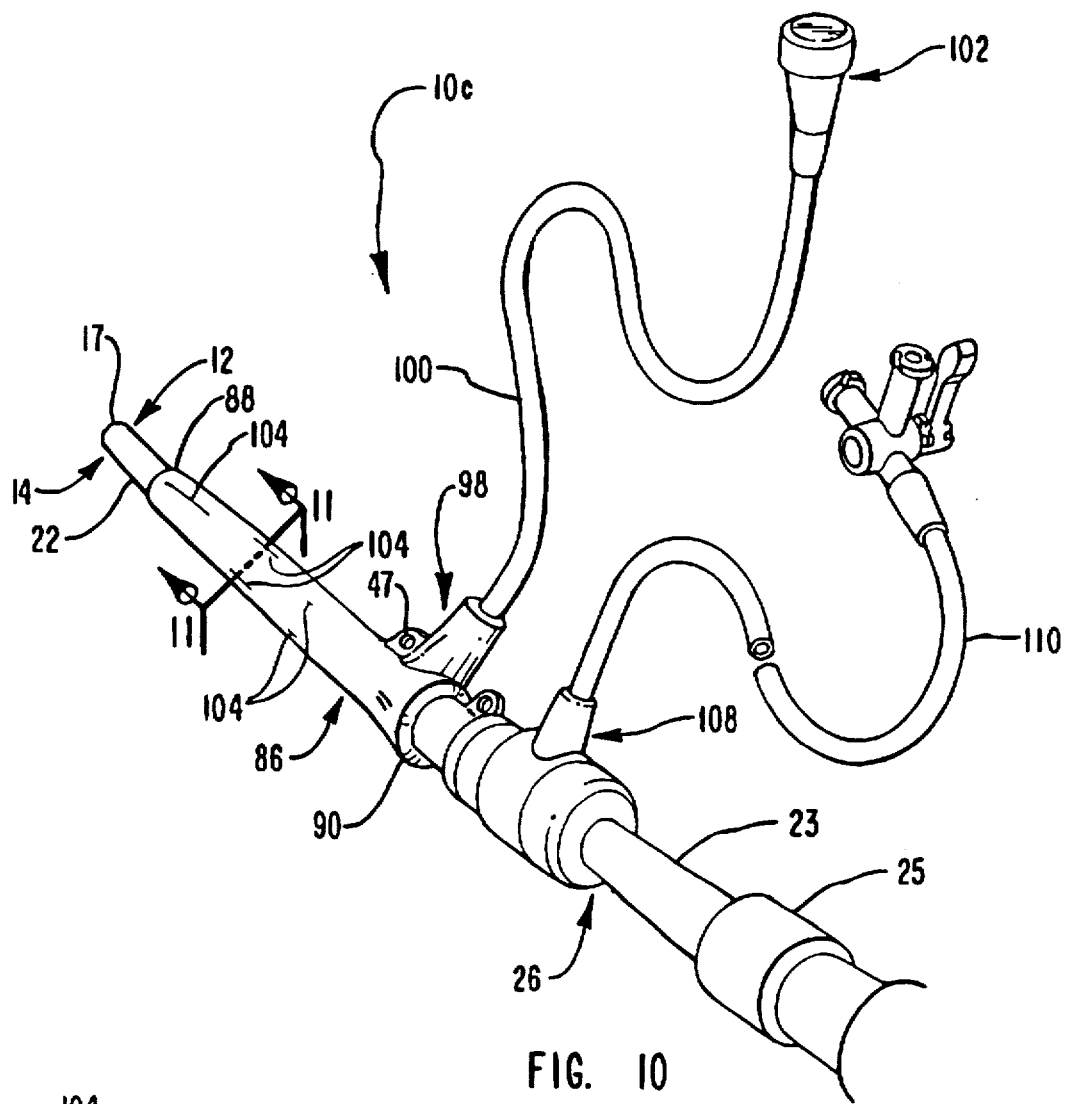
FIG. 10 is a perspective view of the anesthetizing sheath of FIG. 9 mounted to a catheter device.
Figure 11:
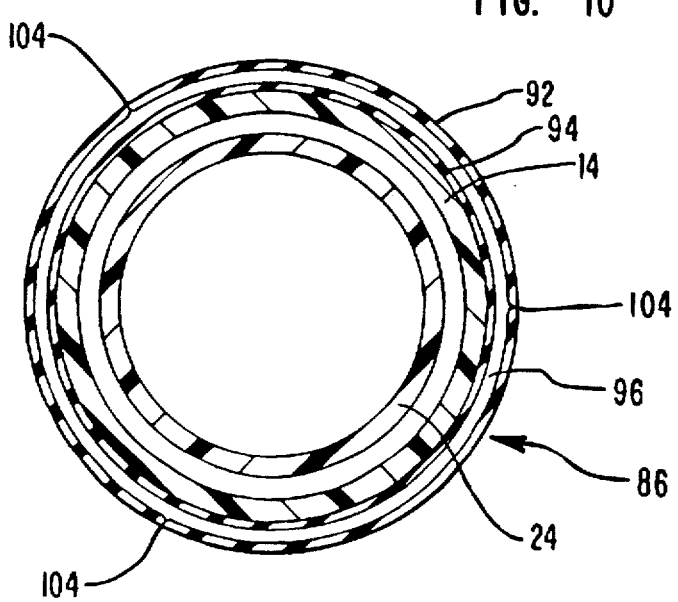
FIG. 11 is a cross-sectional view taken along line 11—11 of FIG. 10.

Yet another embodiment of the indwelling catheter apparatus of present invention is illustrated in FIGS. 9 through 11, and is designated generally at 10c. Indwelling catheter apparatus 10c also includes a catheter means as for example a catheter device, which is essentially the same as the catheter device discussed in conjunction with FIGS. 1 through 3.

The indwelling catheter apparatus 10c also comprises a sheath means as for example a hollow cylindrical sleeve 86, for placement onto at least a portion of the cannula 14 at a point intermediate of the distal end 17 and the proximal hub end 26 of the cannula 14. As with the embodiment shown in FIGS. 6 through 8, the sheath means of FIGS. 9 through 11 can be selectively attached and detached to the cannula 14, as will be discussed in further detail below.

As is shown in FIGS. 9 and 10, cylindrical sleeve 86 has a distal 88 and a proximal end 90. Hollow cylindrical sleeve 86 further has an inner diameter which is greater than the outer diameter of cannula 14. This relationship is also shown in the cross-sectional view of FIG. 11. Also shown in FIG. 11 is cylindrical sleeve 86 positioned in a tight fitting manner on cannula 14 so as to be concentric with the cannula 14. Preferably, distal end 88 of cylindrical sleeve 86 is tapered with respect to the outer surface of cannula 14, so that the cylindrical sleeve 86 can be inserted with little or no trauma through the portion of subcutaneous tissue 20 when it is mounted to the cannula 14.

The cylindrical sleeve 86 further comprises a means for delivering fluid medicament, such as an anesthetic agent (not shown), to the subcutaneous tissue 20 surrounding the sleeve 86. The fluid medicament delivering means comprises, for example, a means for defining an interior lumen running from the distal end 88 to the proximal end 90 of the sleeve 86, a hub means through which the fluid medicament is delivered to the interior lumen, and a plurality of one way valve means for communicating the fluid medicament from the interior lumen to the subcutaneous tissue surrounding the sheath means and for preventing fluids from entering the interior lumen.

By way of example, and referring now to FIG. 11, cylindrical sleeve 86 is illustrated as being comprised of a cylindrical outer wall 92 that is formed over a concentric cylindrical inner wall 94 in a spaced apart relationship. Thus, in this embodiment, interior lumen 96 is provided by the space which is formed between the outer wall 92 and the inner wall 94.

By way of further example and with reference now to FIGS. 9 and 10 in combination, the hub means is comprised of a first hub 98 joined in a fluid tight manner to the proximal end 90 of the cylindrical sleeve 86. First hub 98 further comprises, for example, a first passageway means such as a first hub lumen (not shown), for communicating the fluid medicament to the interior lumen 96. As is shown in FIGS. 9 and 10, the first hub 98 can be attached, for example, to an external tube 100 through which the fluid medicament can be introduced to the internal lumen 96, as for example by syringe (not shown), via an infusion port 102.

FIGS. 9 through 11 further illustrate an embodiment of the plurality of one way valve means spaced along the cylindrical sleeve 86. As is shown, each valve means is comprised of a one way slit 104 that is formed through outer wall 92 of cylindrical sleeve 86. These slits 104 are preferably substantially identical to the one way slits 48 described above in connection with FIGS. 1 through 3.

As is further shown in FIGS. 9 and 10, in this particular embodiment the sleeve 86 is further comprised of a means for selectively attaching and detaching the cylindrical sleeve 86 from the cannula 14. For example, selective attachment and detachment is illustrated as being accomplished by longitudinally sliding the hollow cylindrical sleeve 86 onto cannula 14. The cylindrical sleeve 86 in such a mounted position is illustrated in FIGS. 10 and 11.

When cylindrical sleeve 86 is thus mounted to cannula 14, the cylindrical inner wall 94 is in a continuous and tight fitting contact with the outer surface of cannula 14. The inner diameter of the cylindrical sleeve 86 with respect to the outer diameter of cannula 14 is such that the sleeve 86 remains positioned on the cannula 14 in a slidable, yet tight fitting manner.

The sleeve 86 of this embodiment is also comprised of a means for sealing the sleeve 86 in a fluid tight manner around the cannula 14 so as to prevent fluids, such as blood from the body, from escaping between the cannula 14 and the sleeve 86. For example, as is shown in FIG. 9, this sealing means is accomplished by placing an O-ring 106 between the inner surface of the cylindrical sleeve 86 and the outer surface of the cannula 14. Thus, when the cylindrical sleeve 86 is mounted to the cannula 14, O-ring 106 forms a fluid-tight seal, and thereby prevents any bodily fluids from leaking between sleeve 86 and cannula 14. Cylindrical sleeve 86 also has formed thereon a suture attachment ring 47, similar to the ring 47 discussed above in connection with FIGS. 1 through 3.

In the embodiment of FIGS. 9 and 10, the indwelling catheter apparatus further includes a second hub means as for example hub 108, for providing fluid communication to the cannula 14. Hub 108 is joined in a fluid tight manner to proximal hub end 26 of cannula 14. As is also shown, hub 108 can be connected to external tube 110, through which fluids may be infused to cannula 14.

As discussed, the cylindrical sleeves 56, 86 of the two embodiments of FIGS. 6 through 8 and 9 through 11 are not permanently mounted to any particular catheter device 12, but can be selectively attached and detached to preexisting catheter devices. Consequently, the versatility of a single cylindrical sleeve is greatly enhanced because it can be used with any one of a variety of catheter devices that are already on hand. Thus, when using a preexisting catheter device, medical personnel can retrofit the device with a cylindrical sleeve discussed in connection with FIGS. 6 through 11, and provide the patient with the pain relief that would not otherwise be available with that catheter device. Importantly, this retrofit capability provides the advantages of pain relief, yet simultaneously protects any investment already made in a stock of preexisting catheter devices.

It will be appreciated that although the only difference between the embodiment of FIGS. 6 through 8 and the embodiment of FIGS. 9 through 11 lies in how the cylindrical sleeve 56 or 86 is attached and detached to the cannula 14, the difference in how the two embodiments are used is more significant. In use, cylindrical sleeve 56 (FIGS. 6–8) attaches and detaches to the cannula 14 by way of the longitudinal slit 68 formed along the length of the sleeve 56. Thus, the sleeve 56 can be attached to a cannula 14 even if the cannula 14 has already been inserted in the patient. For instance, a doctor may insert a catheter device, such as an insertion sheath, perform the underlying procedure and, when completed, snap on the cylindrical sleeve 56 to the proximate portion of the cannula 14. Since the patient is still locally anesthetized from the previously performed medical procedure, the sleeve 56 can then be inserted into the portion of subcutaneous tissue 20 with the cannula 14. When the cannula 14 is later retracted (and the previously administered local anesthetic has worn off) the doctor can readminister a local anesthetic to the subcutaneous tissue 20 through sleeve 56 and then painlessly retract the cannula 14. In this way, the doctor or medical technician is not distracted by the extra equipment, tubes, infusion ports, etc. associated with cylindrical sleeve 56 while the underlying medical procedure, such as a PTCA, is being done.

In contrast, cylindrical sleeve 86 (FIGS. 9–11) attaches and detaches to the cannula 14 by sliding the sleeve 86 onto the cannula 14. Consequently, the sleeve 86 of this embodiment cannot be placed on a cannula 14 that has already been inserted in a patient, and must necessarily be positioned on the cannula 14 before the underlying medical procedure is done and thus before cannula 14 is initially inserted into the patient. However, under certain circumstances this approach may be entirely acceptable and/or desirable.

Figure 12:
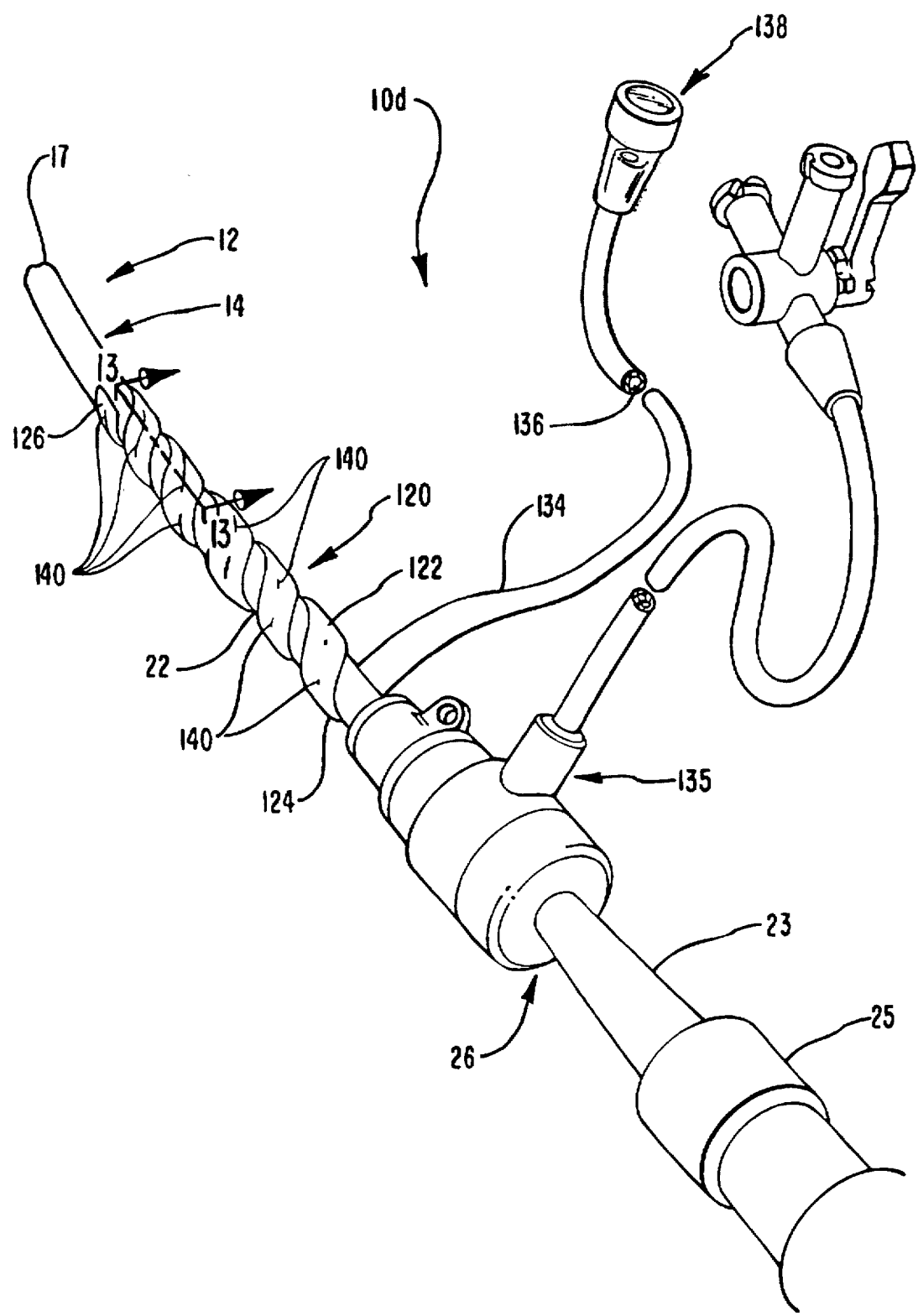
FIG. 12 is a perspective view of still another embodiment of the present invention.
Figure 13:
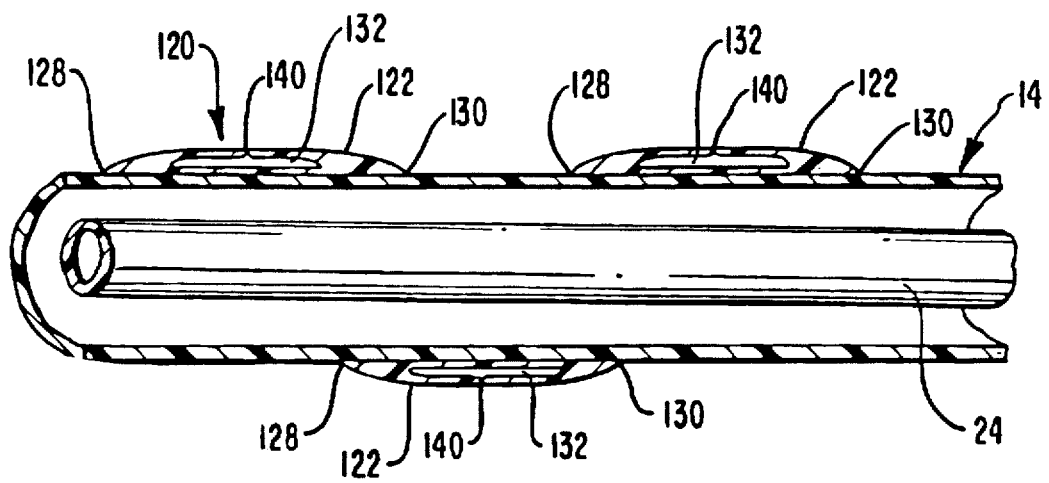
FIG. 13 is an enlarged cross-sectional view taken along lines 13—13 of FIG. 12.

FIGS. 12 and 13 illustrate yet another embodiment of the indwelling catheter apparatus of the present invention, designated generally at 10d. As in the embodiments previously discussed, catheter apparatus 10d includes a catheter means as for example a catheter device, which is essentially the same as the catheter device of the previous embodiments.

The indwelling catheter apparatus 10d also has a sheath means for placement onto the cannula 14. By way of example and referring now to FIG. 12, sheath means is comprised of a helical sheath, designated generally at 120. As is shown, helical sheath 120 is comprised of a single band 122 that is wound in a helical fashion so as to conform to the cylindrical outer periphery of the cannula 14. The helical sheath 120 has a proximate end 124 and a distal end 126, and is preferably positioned on the cannula 14 so that it can be disposed within the area of subcutaneous tissue 20 in conjunction with the cannula 14 (in the same manner illustrated in FIG. 2).

Referring now to FIG. 13, the band 122 that forms helical sheath 120 has a substantially flat cross-section when it is placed on the cannula 14. Further, when positioned on the cannula 14, band 122 has successive leading edges 128 and trailing edges 130 that are tapered with respect to the outer surface of the cannula 14. Advantageously, when the helical sheath 120 is mounted to the cannula 14, this flat cross-section and the tapered leading and trailing edges 128, 130 of band 122 act so as to ease the insertion and retraction of the helical sheath 120 through the patient's skin and subcutaneous tissue 20 when it is mounted to the cannula 14. Similarly, this configuration minimizes trauma to the skin or subcutaneous tissue 20 when the helical sheath 120 is inserted and retracted.

Figure 13A:
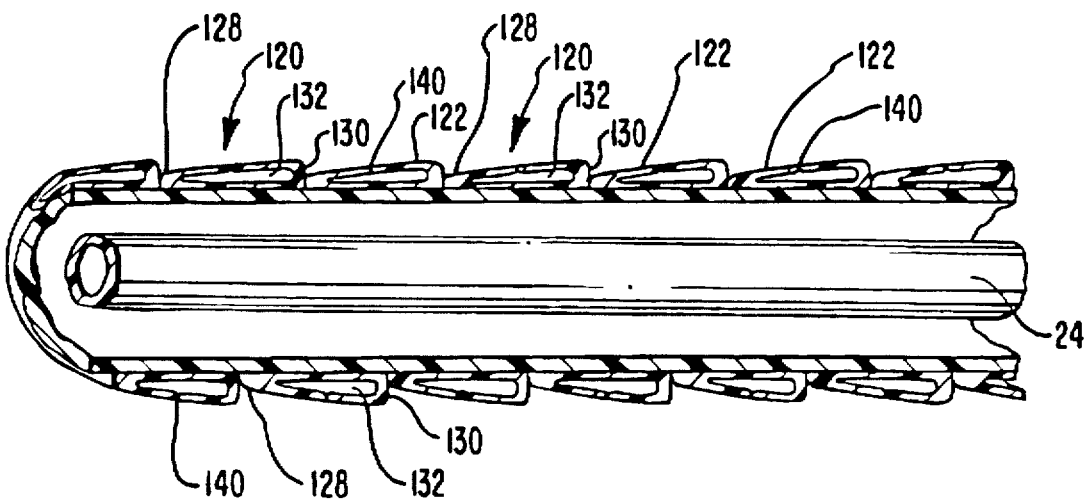
FIG. 13A is an enlarged cross-sectional view showing an alternative embodiment of the catheter apparatus of FIG. 12.

Alternatively, FIG. 13A illustrates another cross-sectional shape that may be formed by band 122. In this embodiment, band 122 is placed on cannula 14 in a tight helical fashion such that the leading edges 128 abut against the adjacent trailing edges 130. Further, each leading edge 128 slopes upwardly towards the trailing edge 130 to form an overall tapered shape. In this way, the helical sheath 120 has an overall tapered shape so as to permit easier insertion through the patient's skin and subcutaneous tissue 20.

Helical sheath 120 is further comprised of a fluid medicament delivery means for delivering a fluid medicament, such as an anesthetic agent, to the subcutaneous tissue 20 in which the helical sheath 120 is disposed. By way of example, FIGS. 12 and 13 illustrate how the fluid medicament delivery means is preferably comprised of a means for defining an interior lumen running from the distal end 126 to the proximal end 124 of helical sheath 120. As is shown, lumen means is comprised of an interior lumen 132 that is defined by a hollow portion formed within band 122. The hollow portion that defines interior lumen 132 extends along the entire length of helical sheath 120.

Helical sheath 120 is also preferably comprised of a hub means through which the anesthetic agent is delivered to the interior lumen 132. As FIG. 12 illustrates, hub means is comprised, for example, of a tube 134 which is coupled in a fluid tight manner to the proximal end 124 of the helical sheath 120. Tube 134 has a single lumen 136 that is in fluid communication with the interior lumen 132. Anesthetic agent can be delivered to interior lumen 132 through a fluid injection port 138 connected to the opposite end of tube 134. FIG. 12 further illustrates how hub means also comprises, for example, a hub 135 that is connected in a fluid tight manner to the proximal hub end 26 of cannula 14. Hub 135 is essentially identical to hub 108 discussed in connection with the embodiment of FIG. 10, and thus that discussion will not be repeated.

With continued reference to FIG. 12, helical sheath 120 also comprises a plurality of one way valve means for communicating the anesthetic agent from the interior lumen 132 to the subcutaneous tissue 20 surrounding the sheath 120, and at the same time, for preventing bodily fluids, such as blood, from entering the interior lumen 132. For example, FIGS. 12 and 13 illustrate how the valve means are each comprised of a one way slit 140 that is formed through the band 122 to interior lumen 132. One way slits 140 are placed uniformly along helical sheath 120, and are essentially identical to the one way slits discussed above in connection with the embodiments of FIGS. 1 through 11.

As discussed generally, helical sheath 120 may further comprise a means for selectively attaching and detaching the helical sheath 120 to the cannula 22. This function is provided by wrapping the helical sheath 120 onto the longitudinal length of cannula 14 so that the helical sheath 120 is concentrically positioned on the cannula, as is illustrated in FIG. 12. It will be appreciated that, like the embodiment of FIGS. 6 through 8, helical sheath 120 can be detachably mounted to a cannula 14 even after the cannula 14 has already been inserted into the patient. Preferably, the helical sheath 120 exhibits sufficient resilient properties such that once it is positioned on the cannula 14, it remains positioned in a tight fitting manner. Alternatively, once helical sheath 120 has been detachably mounted to the cannula 14, the medical technician may further adhere the sheath 120 to the cannula 14 by applying a small amount of liquid adhesive. Thus, helical sheath 120 can be selectively used on a variety of preexisting catheter devices. Alternatively, cannula 14 can be manufactured with a helical sheath 120 premounted in the manner illustrated in FIG. 12. In this instance, helical sheath 120 would be affixed permanently to the catheter device 12 by fusing, or similarly adhering it to the cannula 14.

Figure 14:
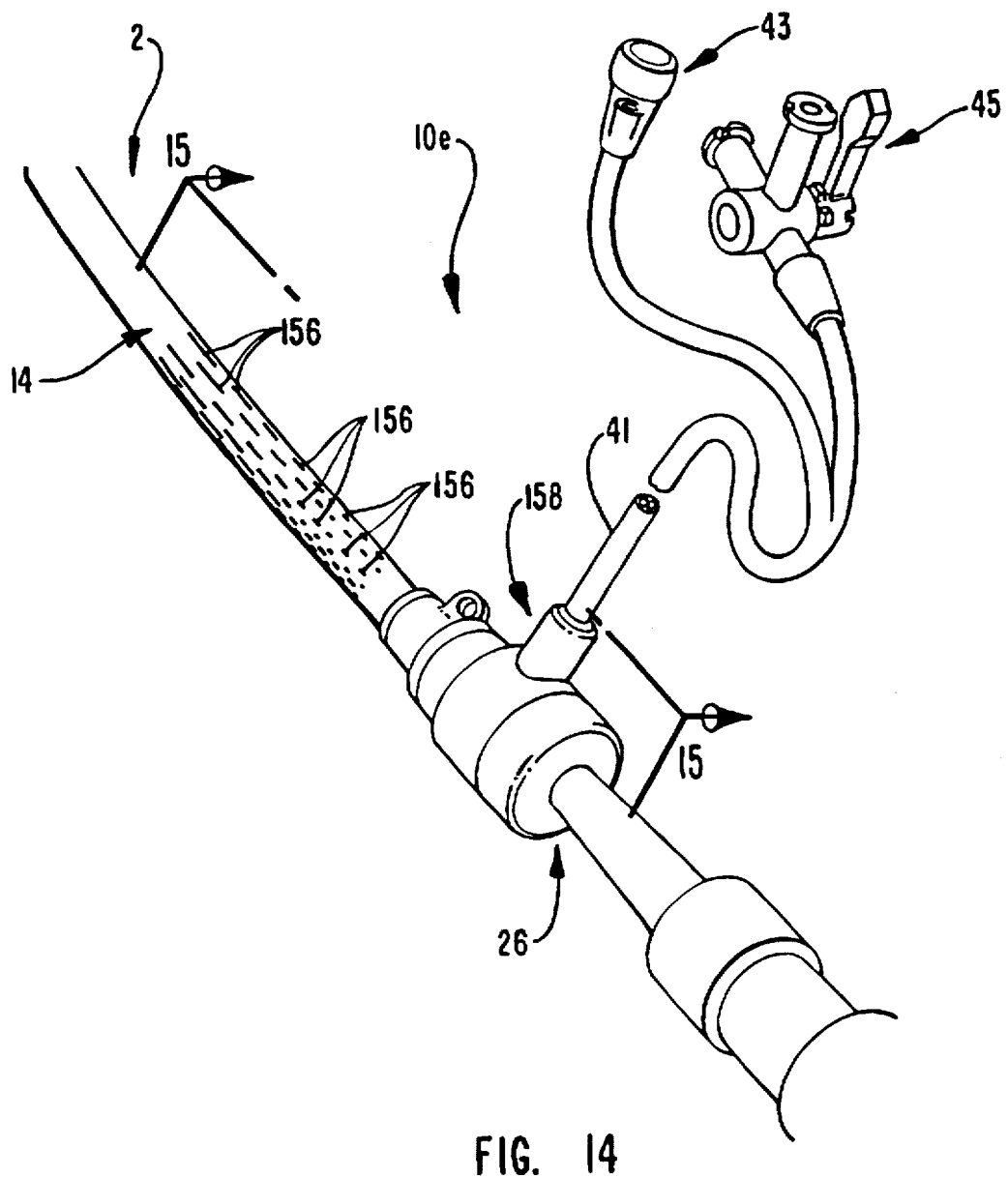
FIG. 14 is a perspective view of yet another embodiment of a catheter apparatus constructed in accordance with the inventive concepts of the present invention.
Figure 15:
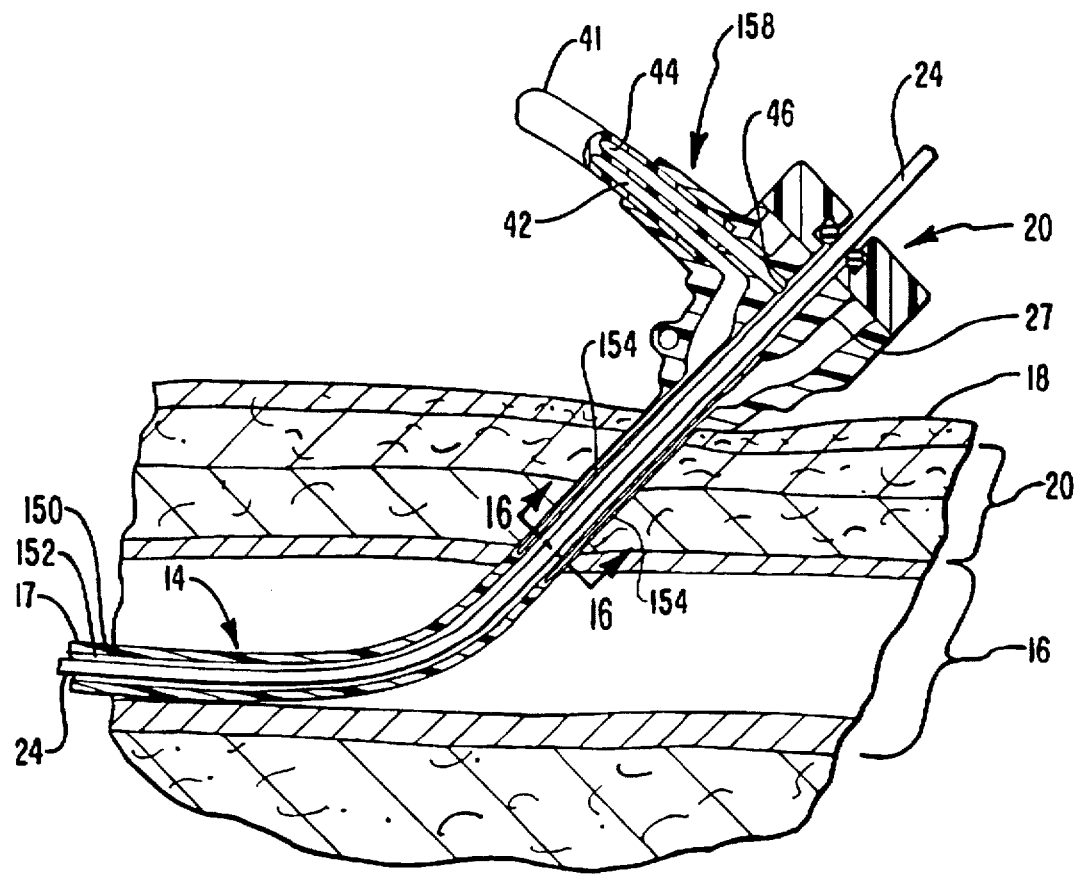
FIG. 15 is a cross-sectional view taken along lines 15—15 of FIG. 14, and further illustrates the catheter apparatus of FIG. 14 disposed within a portion of a patient's body.
Figure 16:
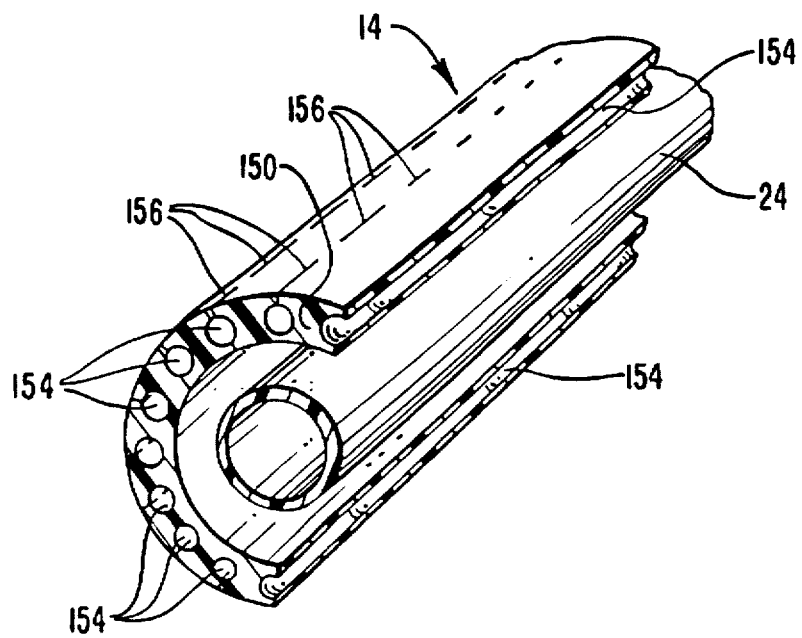
FIG. 16 is an enlarged cross-sectional view taken along lines 16—16 of FIG. 15.

Referring now to FIGS. 14 through 16, yet another embodiment of indwelling catheter apparatus, designated generally at 10e, is shown. Indwelling catheter apparatus 10e includes a catheter means as for example a catheter device 12, that has a cannula 14 for insertion through subcutaneous tissue 20 into a patient's body (shown in FIG. 15). The catheter device 12 is essentially identical to the catheter device described in conjunction with the previous embodiments, having an indwelling distal end 17 and a proximal hub end 26. FIG. 15 further illustrates how cannula 14 is a cylindrical tube having a cylindrical outer wall 150, through which a primary lumen 152 runs.

Indwelling catheter apparatus 10e also comprises a means for delivering a fluid medicament, such as an anesthetic agent, to essentially only the area of subcutaneous tissue 20 through which the cannula 14 is inserted. For example, in the embodiment of FIGS. 14 through 16, the means for delivering a anesthetic agent is comprised of a secondary lumen that is formed in the outer wall 150 of the cannula 14. FIGS. 15 and 16 illustrate how the secondary lumen is preferably comprised of a plurality of longitudinal bores 154 formed within the outer wall 150, as is further shown, the plurality of bores 154 are uniformly spaced about the circumference of the cannula 14, and each bore 154 is substantially parallel to the primary lumen 152 running through the cannula 14. Further, the plurality of bores 154 that form the secondary lumen are preferably formed in the cannula 14 outer wall 150 so that they are substantially disposed within the area of subcutaneous tissue 20 once the cannula 14 has been inserted within the patient's body. In this way, secondary lumen, as defined by the plurality of bores 154, can distribute the anesthetic agent to the subcutaneous tissue 20 evenly and uniformly.

The anesthetic agent is communicated to the surrounding subcutaneous tissue 20 from the secondary lumen 154 through a plurality of one way valve mean which also act to prevent bodily fluids from entering the secondary lumen 154. As FIG. 14 illustrates, the one way valve means are each comprised of a single one way slit 156 that is formed through the outer wall 150 to each of the plurality of longitudinal bores 154. This is illustrated in further detail in the exploded cross-section view of FIG. 16, where one way slits 156 are illustrated. Each of the one way slits 156 are substantially identical to the one way slits discussed above in connection with the other embodiments.

To deliver the anesthetic agent to the secondary lumen 154, the fluid medicament delivery means is further comprised of a hub means. This hub means is illustrated as being comprised of a single hub 158, that is joined in a fluid tight manner to the proximal hub end portion 27 of the cannula 14. FIGS. 14 and 15 illustrate how hub 158 is formed with a first hub lumen 42 and a second hub lumen 44. First hub lumen 42 is coupled to each of the longitudinal bores 154 that form the secondary lumen so as to provide a passageway for delivering anesthetic agent. Similarly, second hub lumen 44 is coupled to the primary lumen 152 via a cannula access hole 46, thereby providing a separate fluid passageway for that lumen. As FIG. 14 illustrates, the first and second hub lumens 42, 44 are connected to a multi-lumen tube 41, through which the first hub lumen 42 is connected to an infusion port 43, and second hub lumen 44 is connected to an I.V. valve assembly 45. Thus, anesthetic agent can be delivered to the bores 154 that form the secondary lumen with a syringe by using infusion port 43.

Figure 17A:
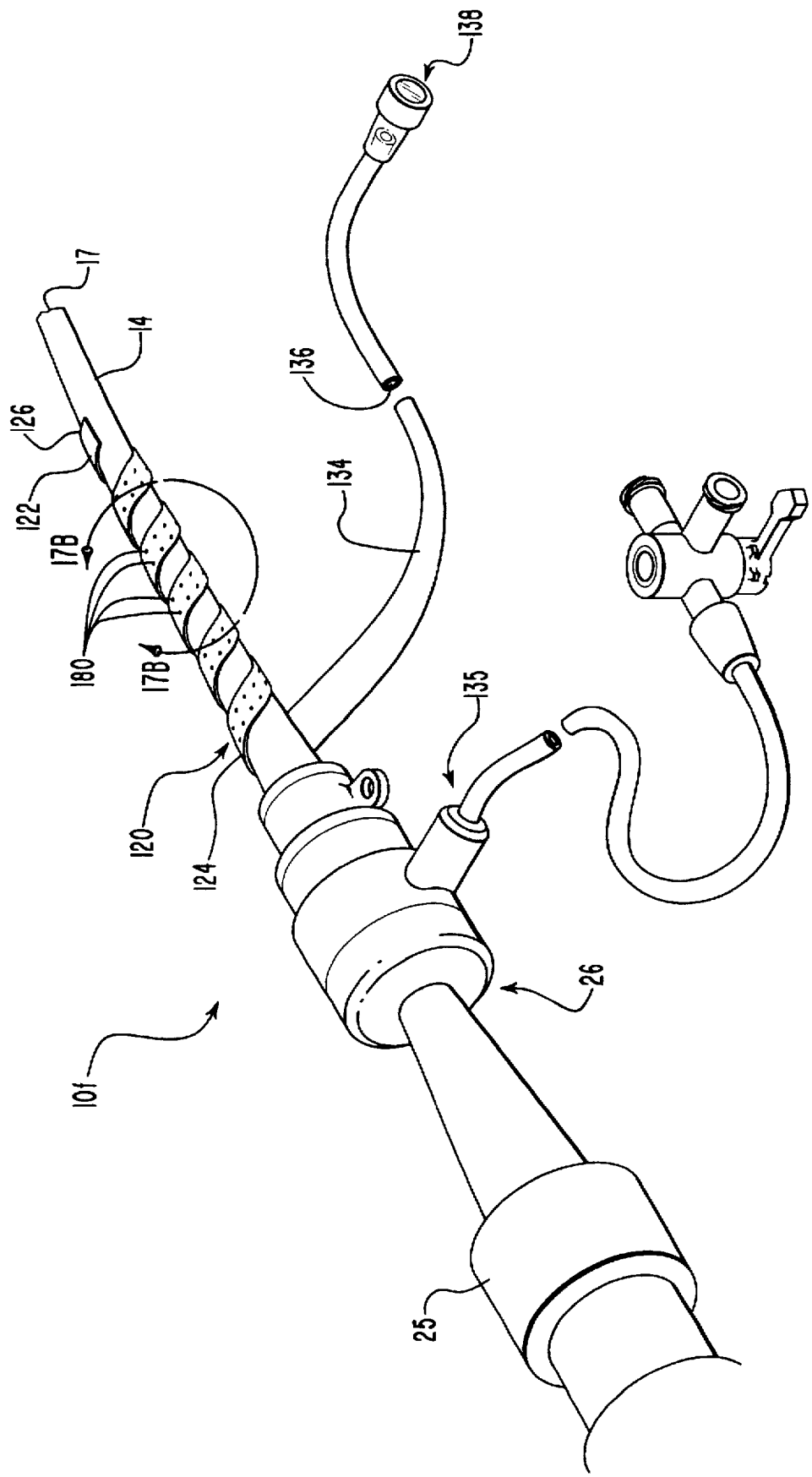
FIG. 17A is a perspective view of yet another embodiment of the anesthetizing sheath mounted to a catheter device.

Referring next to FIGS. 17A-B and 18A-B, yet another embodiment of the present invention is shown. FIG. 17A illustrates an indwelling catheter apparatus 10f having a sheath means that is comprised of a hollow elongate band, wrapped in a helical fashion about cannula 14. This helical sheath, designated generally at 120, is substantially identical to the helical sheath 120 shown in FIG. 12. The identical portions of that device are designated with like numerals in FIG. 17A, and their description will not be repeated. However the embodiment of FIG. 17A differs from that of FIG. 12 in the manner by which the valve means is constructed.

Figure 17B:
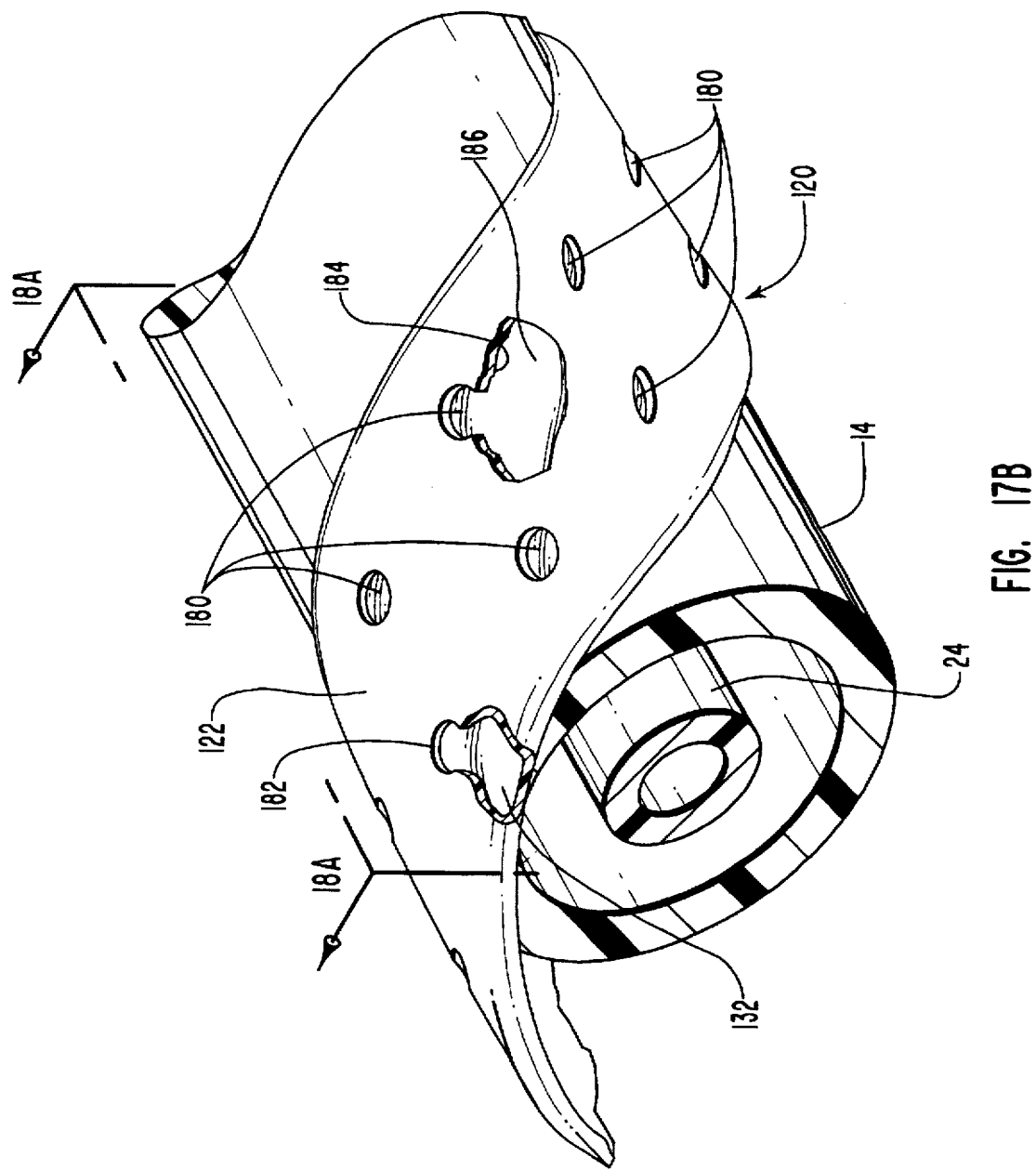
FIG. 17B is an enlarged perspective view in partial cross-section taken along lines 17B—17B of FIG. 17A.
Figure 18A:
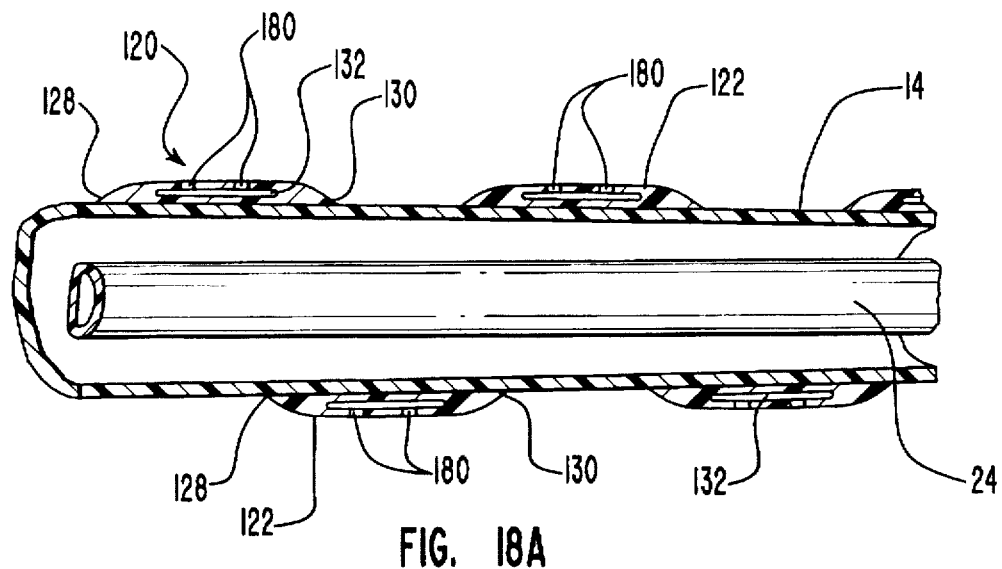
FIG. 18A is an enlarged cross-sectional view taken along lines 18A—18A of FIG. 17B.
Figure 18B:
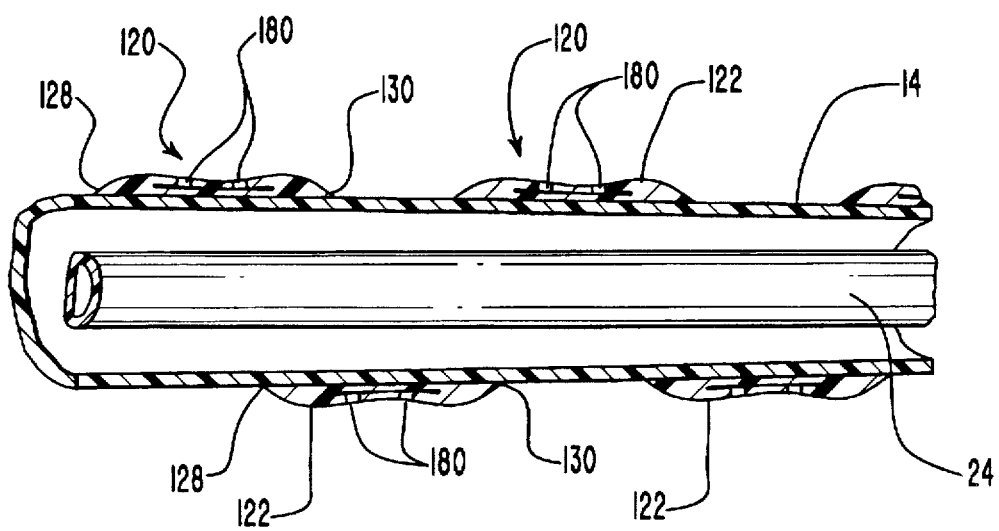
FIG. 18B is an enlarged cross-sectional view also taken along lines 18A—18A of FIG. 17B, illustrating the manner by which the interior lumen is compressed so as to close the delivery holes and thereby prevent the entry of bodily fluids into the lumen.

As is shown by way of example in FIG. 17A, in this particular embodiment the valve means is comprised of a plurality of delivery holes, designated at 180, which are substantially circular in shape and arranged uniformly along the length of the elongate band 122 that forms the helical sheath 120. FIG. 17B illustrates in further detail how each circular hole 180 is formed completely through the outer surface 182 of the band 122 so as to provide a fluid communication path with the interior lumen 132 formed within the band 122. Each hole 180 acts as a fluid path for delivering the anesthetic agent, or similar fluid medicament, to the subcutaneous tissue that is coextensive with the helical sheath 120 when it is inserted into the patient.

The helical sheath 120 may be constructed of a slightly flexible material, such as a polyurethane, Teflon, polyethylene, or similarly flexible and medically suitable material. When fluid medicament is to be delivered to the subcutaneous tissue 20 of a patient, a positive fluid pressure is generated within the interior lumen 132, as for example by way of a syringe (not shown) that is connected to the injection port 138. In this pressurized state, illustrated in cross-section in FIG. 18A, the interior lumen 132 expands and thereby opens each of the holes 180. In this "open state," fluid medicament is delivered from the interior lumen 132, through the open delivery holes 180, and to the subcutaneous tissue 20.

The delivery holes 180 also prevent bodily fluids and/or fluid medicament from reentering the interior lumen 132. The flexibility of the material used to form the helical sheath 120 and the size of the holes 180 together act to perform this function. When the sheath 120 is positioned within the subcutaneous tissue 20 and medicament is not being delivered, there is no fluid pressure present within the lumen 132. Instead, the pressure exerted on the exterior surface 182 of the sheath 120, such as that which would be caused by the surrounding subcutaneous tissue 20 and the interstitial blood pressure, compresses the interior lumen 132 and causes the lumen walls 184, 186 (shown in FIG. 17B) to collapse against one another. This condition is best seen in the cross-sectional illustration of FIG. 18B. As is shown in this compressed state, the delivery holes 180 no longer provide a fluid communication path to the interior lumen 132, and external bodily fluids are thereby prevented from entering the lumen 132.

In one embodiment, each of the delivery holes 180 are generally circular in shape, and are all of the same approximate diameter. However, it will be appreciated that the holes 180 can have various different shapes and yet provide the function described above. Also, if desired the hole 180 sizes can be varied, thereby controlling the amount of medicament that is delivered to the subcutaneous tissue 20.

Also, although this embodiment discloses the use of delivery holes 180 on a helical sheath 120, it will be appreciated that the holes 180 could also be used in conjunction with the other sheath embodiments described herein.

Yet another embodiment of the indwelling catheter apparatus of the present invention is illustrated in FIGS. 19 through 23, and is designated generally at 10g. Indwelling catheter apparatus 10g also includes a catheter means as for example a catheter device, which is essentially the same as the catheter device discussed in conjunction with FIGS. 1 through 3.

The indwelling catheter apparatus 10g also comprises a sheath means as for example a hollow cylindrical sleeve 190, for placement onto at least a portion of the cannula 14 at a point intermediate of the distal end 17 and the proximal hub end 26 of the cannula 14. The sheath means of FIGS. 19 through 23 can also be selectively attached and detached to the cannula 14, as will be discussed in further detail below.

Figure 19:
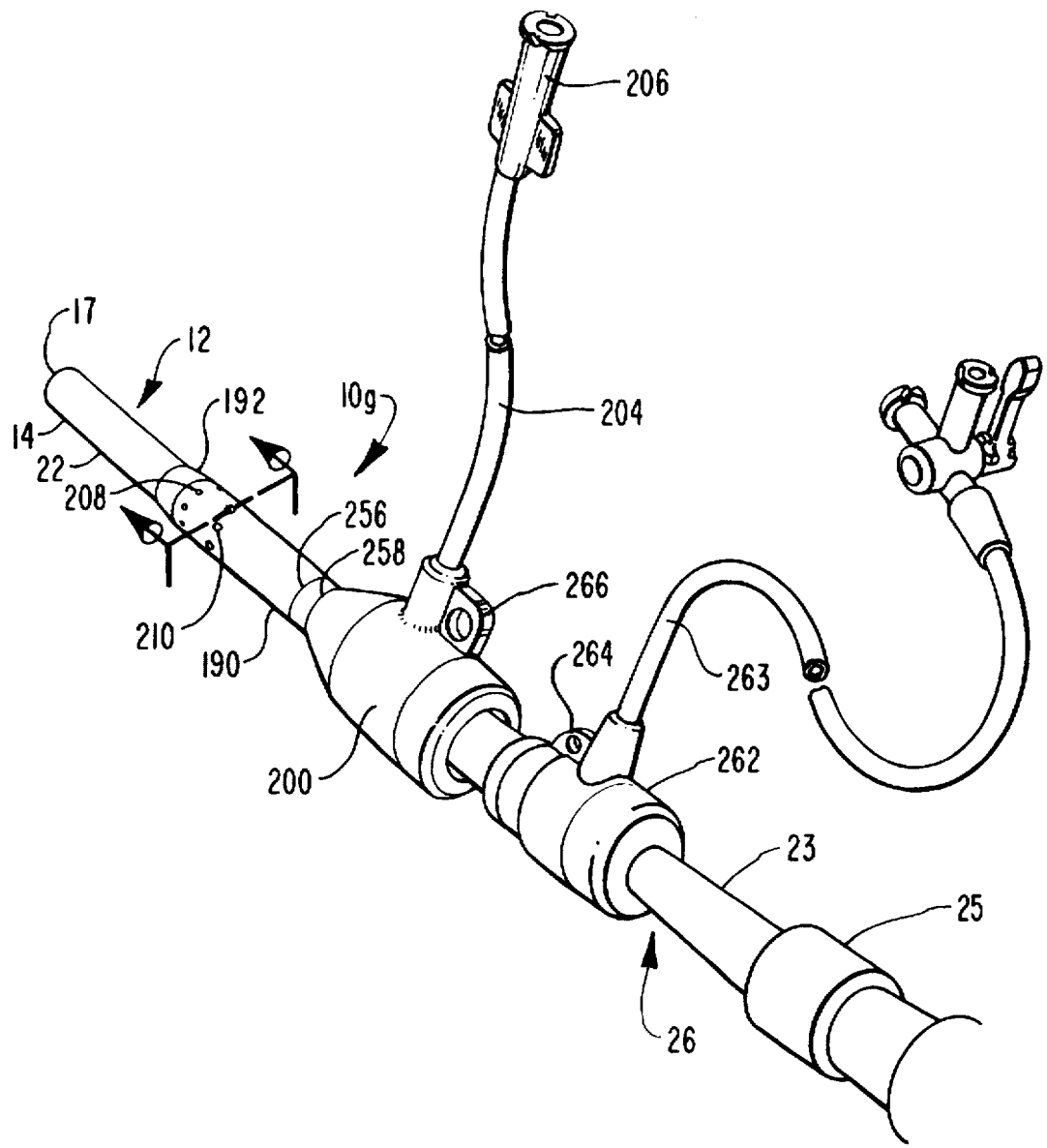
FIG. 19 is a perspective view of yet another embodiment of the invention including a light-permeable hub.
Figure 20:
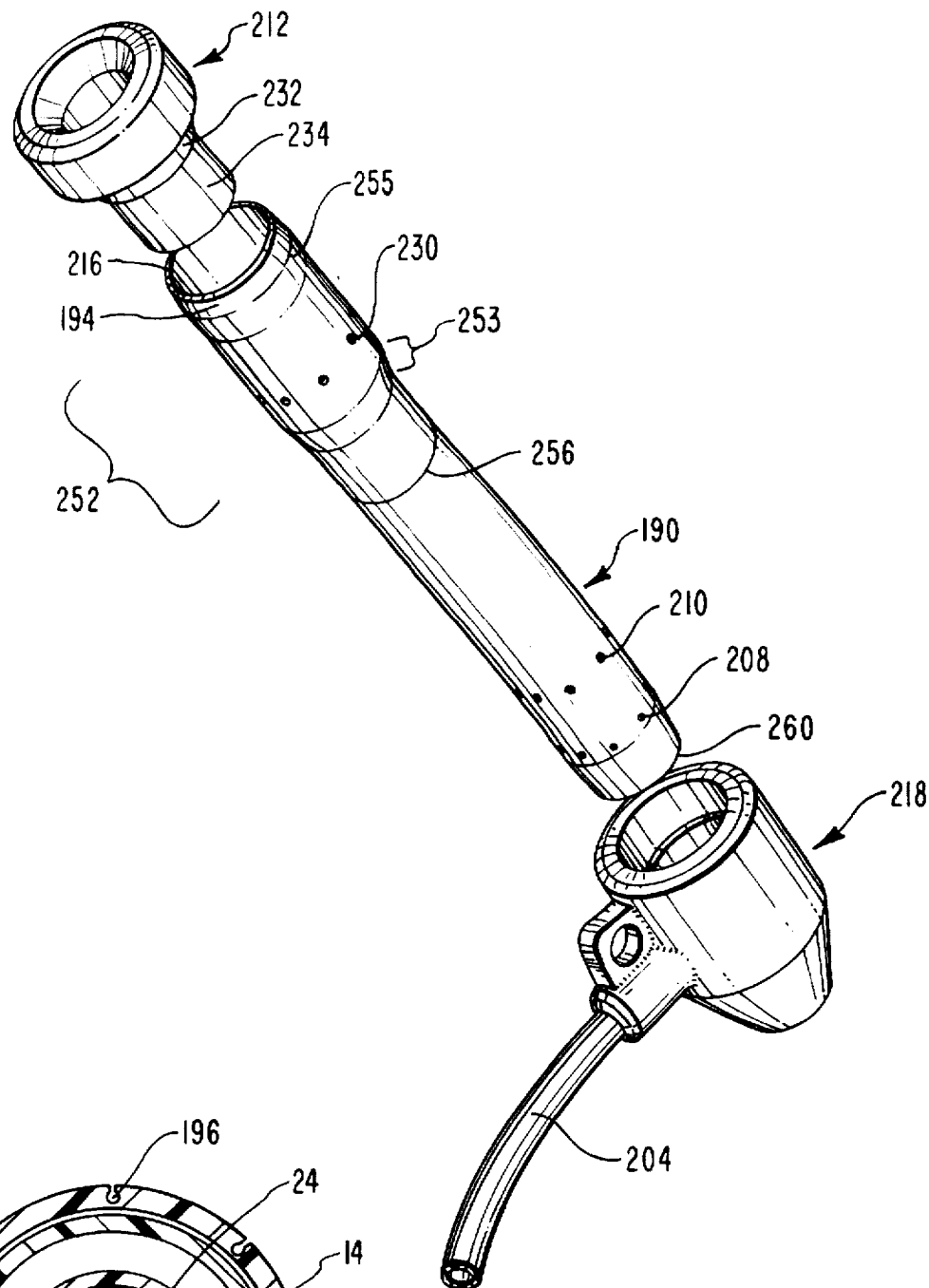
FIG. 20 demonstrates the main components of an unassembled hub of FIG. 19.
Figure 21:
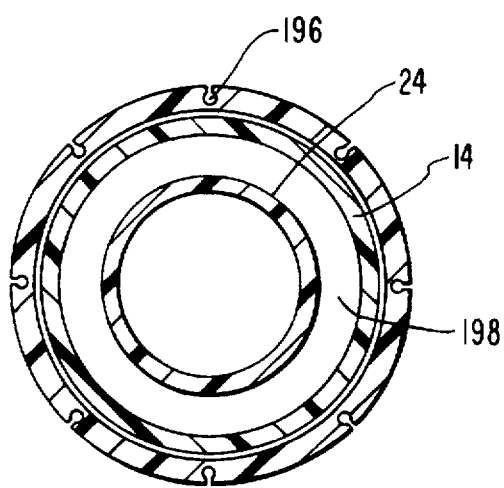
FIG. 21 is a cross-sectional view taken along line 21—21 of FIG. 19.
Figure 22:
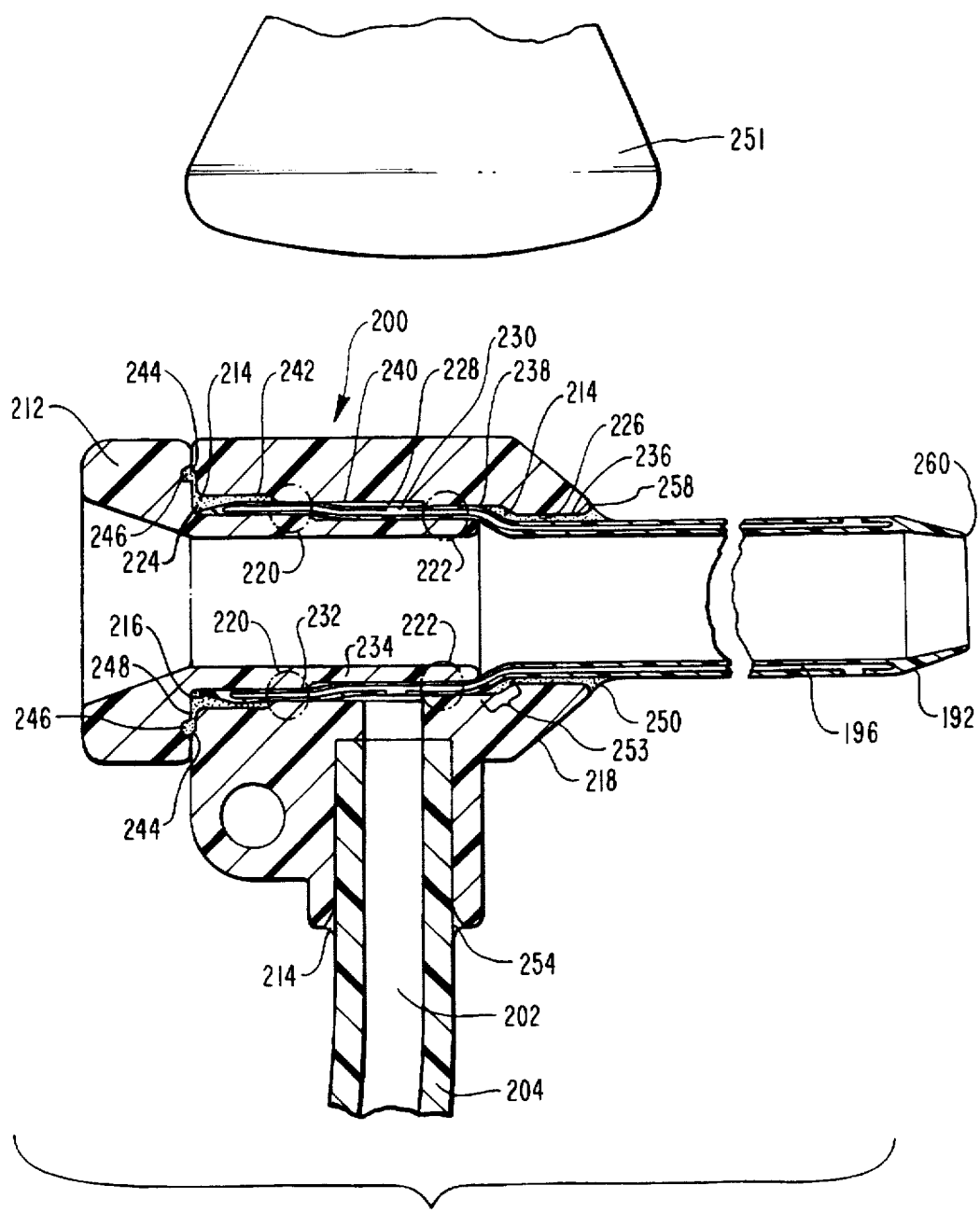
FIG. 22 is a cross-sectional view of the assembled hub illustrated in FIG. 19, illustrating the annular raceways in which adhesive may be disposed and the annular raceway or cavity in which fluid medicament may be disposed.

As is shown in FIGS. 19 and 20, cylindrical sleeve 190 has a distal end 192 and a proximal end 194. As shown in FIG. 21, generally, cylindrical sleeve 190 is positioned so as to be concentric, but not necessarily tight-fitting with the cannula 14. While a tight-fitting relationship at the location shown in FIG. 21 is possible, it is not currently preferred. Instead, distal end 192 of cylindrical sleeve 190 is tapered as shown in FIG. 22, so that the distal end 192 is tight fit about the cannula 14 and so that cylindrical sleeve 190 can be inserted with little or no trauma through the portion of subcutaneous tissue when it is mounted to the cannula 14.

The distal end 192 thus acts as a means for sealing the sleeve 190 in a fluid tight manner around the cannula 14 so as to prevent fluids, such as blood from the body, from escaping between the cannula 14 and the sleeve 190. The outer surface of the proximal end 194 is also preferably tapered, as shown in FIG. 20.

The cylindrical sleeve 190 further comprises a means for delivering fluid medicament, such as an anesthetic agent (not shown), to the subcutaneous tissue surrounding the sleeve 190. The fluid medicament delivery means comprises, for example, a means for defining an interior lumen running from the sealed distal end 192 to the sealed proximal end 194 of the sleeve 190, a hub means through which the fluid medicament is delivered to the interior lumen, and a plurality of valve means for communicating the fluid medicament from the interior lumen to the subcutaneous tissue surrounding the sheath means.

By way of example, and referring now to FIG. 21, the interior lumen of sleeve 190 is comprised of a plurality of longitudinal bores 196 (preferably eight) formed and uniformly spaced within the sleeve 190. Each bore 196 is substantially parallel to a primary lumen 198 running through the cannula 14.

By way of further example and with reference now to FIGS. 19 through 22 in combination, the hub means is comprised of a first hub 200 joined in a fluid tight manner to the cylindrical sleeve 190. First hub 200 further comprises, for example, a first passageway means such as a first hub lumen 202 for communicating the fluid medicament to the plurality of longitudinal bores 196. As is shown in FIG. 19, the first hub 200 can be attached, for example, to an external tube 204 through which the fluid medicament can be introduced to the plurality of longitudinal bores 196, as for example by syringe (not shown) via an infusion port 206.

FIGS. 19 through 21 further illustrate an embodiment of the plurality of valve means spaced along the cylindrical sleeve 190. As is shown, each valve means is comprised of a delivery hole. Preferably, two sets of delivery holes 208, 210 are disposed within each of eight longitudinal bores 196 for subcutaneous delivery of the fluid medicament such that each longitudinal bore comprises a distal delivery hole 208, and a proximal delivery hole 210. In this embodiment, the delivery holes 208, 210 allow the free flow of fluid out of the delivery hole and into the delivery hole.

When fluid under pressure is exerted out of the holes, significant amounts of blood and other bodily fluids will not be allowed to enter the holes because of the high velocity of spray. However, when the pressure ceases, blood could potentially seep into the holes 208, 210. The advantage of this design is that fluid entering through the delivery holes and into the first hub 200, first hub lumen 202 and/or external tube 204 may act as a signal to the practitioner that the delivery holes 208, 210 have been extended beyond the subcutaneous tissue into a blood vessel. The first hub 200, first hub lumen 202 and/or external tube 204 may be light permeable, i.e. translucent or transparent, such that a practitioner will recognize blood or other bodily fluids flowing from the sheath means into the structure. Each hole and whatever translucent or transparent portion of the catheter apparatus is in direct or indirect fluid communication with the holes, thus serve as an example of a means for regulating the location of the sheath means.

As is further shown in FIG. 19, in this particular embodiment the sleeve 190 is further comprised of a means for selectively attaching and detaching the cylindrical sleeve 190 from the cannula 14. For example, selective attachment and detachment may be accomplished by longitudinally sliding the hollow cylindrical sleeve 190 onto or off the cannula 14.

As discussed, the cylindrical sleeves 56, 86, and 190 of the three embodiments of FIGS. 6 through 8, 9 through 11, and 19 through 23 are not permanently mounted to any particular catheter device 12, but can be selectively attached and detached to preexisting catheter devices. Consequently, the versatility of a single cylindrical sleeve is greatly enhanced because it can be used with any one of a variety of catheter devices that are already on hand. Thus, when using a preexisting catheter device, medical personnel can retrofit the device with such a cylindrical sleeve and provide the patient with the pain relief that would not otherwise be available with that catheter device. Importantly, this retrofit capability provides the advantages of pain relief, yet simultaneously protects any investment already made in a stock of preexisting catheter devices.

It will also be appreciated that cylindrical sleeve 190 may be employed in conjunction with a variety of catheter apparatus embodiments disclosed herein. For example, the cylindrical sleeve 28, disclosed in cross section in FIG. 2 could also include a non-fused distal end and be substituted by cylindrical sleeve 190 or a sleeve similar thereto.

The hub means for each catheter apparatus 10 through 10g disclosed herein may be made from light-permeable components, for example, polycarbonate, such that radiation curable adhesive, such as ultraviolet activated curing adhesive, may be used to create a fluid tight seal within each hub means. By assembling a light-permeable hub means employing ultraviolet-curable adhesive, the hub means can be assembled quickly and with a fluid-tight seal without employing an insert molding process which may melt or otherwise deform the sheath means. While a light-permeable hub may be employed in conjunction with a variety of sheath means, light-permeable hubs are particularly useful when employing sheath means having a separate longitudinal bore or bores which comprise a lumen, such as the cylindrical sleeve 190 shown in cross section in FIG. 21. The use of a variety of longitudinal bores in a lumen structure is a significant advance in the art. The individual bores provide structural support for the lumen, preventing collapse of the sleeve 190 and interior lumen under pressure.

However, individual bores such as the bores 196 demonstrated in FIG. 21 are fragile and subject to melting during an insert molding process which is often used to create a fluid-tight seal. Furthermore, in light of the fact that materials such as nylon are often used as the material for the cylindrical sleeve 190, insert molding may result in the melting and compression or other distortion of the longitudinal bores unless a mandril or similar supporting structure is placed in each of the lumens, which would be complicated, inefficient and expensive in the manufacturing process. Thus, the hub means disclosed throughout this specification, including the first and second hub means of the various embodiments may comprise light-permeable hubs such that they may be sealed using ultraviolet activated adhesive. Polyethylene, polyurethane, and Teflon are other typical examples of materials for sleeve 190.

Close attachment of a sleeve, such as sleeve 190, to the hub means is critical for effective distribution of fluid medicament so that when the sleeve is pressurized, the sleeve will not balloon inward in the region adjacent to the hub, possibly distorting the lumen or lumens. Radiation curable adhesives assist in this process. The adhesive can be placed in the general desired location within the hub, then allowed to wick into the specific desired location, then cured.

While other adhesives could be used, the mechanical bond obtained through the use of non-radiation curable adhesives is achieved less quickly than the bond achieved through the use of radiation curable adhesives. Since it may be preferable to provide a hub which is permeable to light or UV rays, but which masks the fluid within the hub, or is color-coded for identification purposes, a translucent hub may be desirable as opposed to a transparent hub.

To describe the preferred light-permeable hub means in detail, and to illustrate the principles applicable to each hub means embodiment disclosed herein, specific reference will now be made to FIGS. 19 through 23.

The preferred hub means is comprised of a proximal hub means, such as a cylindrical insert 212 and a distal hub means such as hollow cylindrical cover 218, shown in an exploded view in FIG. 20. To assemble the hub means, part of the sheath means is interposed between the proximal and distal hub means. For example, a proximal portion 252 of the sleeve 190 may be disposed about the insert 212, after which the cylindrical cover 218 is disposed about the proximal portion 252, sandwiching the proximal portion 252 between the insert 212 and the cover 218, as shown in cross section in FIG. 22.

With continued reference to FIG. 22, ultraviolet activated adhesive 214 is disposed between portions of the cylindrical cover 218, the cylindrical insert 212, and the disposed proximal portion 252 of the sleeve 190 to retain the hub components together and to retain sleeve 190 within the hub 200. For example, following disposition of the proximal portion 252 on the insert 212, the adhesive 214 may be disposed about portions of the cylindrical insert 212 and the disposed proximal portion 252, after which the cylindrical cover 218 is disposed about the adhesive covered proximal portion 252. In addition, ultraviolet activated adhesive 214 may be (and preferably is) added between portions of the sleeve 190 and a distal portion of the cylindrical cover 218 to prevent the sleeve 190 from ballooning inward during use. The adhesive 214 is then cured.

As shown in FIG. 22, contours of the sleeve-covered cylindrical insert 212 mate with contours of the cylindrical cover 218. Because the mating relationship only occurs in certain regions, annular raceways 224, 226 for the disposition of adhesive are created. A third raceway 228 is also created which is in fluid communication with first hub lumen 202 and with ports 230 (having the shape of holes) in the sleeve 190, allowing fluid to enter and exit the sleeve 190. To create these partial mating relationships, as will be discussed in greater detail below, the cylindrical insert 212 preferably includes an enlarged portion and two reduced diameter portions which receive the proximal portion 252 of the sleeve 190 in mating relationship. The cylindrical cover 218 includes a variety of tiers and is configured to slide over the proximal portion 252 of the sleeve 190 and engage the shoulder 248 of the insert 212 in an abutting relationship, sandwiching the proximal portion 252 of the sleeve 190 between the distal end of the insert 212 and the inner surface of the cover 218.

As shown in cross section in FIG. 22, the proximal sleeve portion 252 is preferably disposed about cylindrical insert 212, after which adhesive 214 is applied to the cylindrical insert 212 and the area surrounding the proximal tip 216 of the cylindrical sleeve 190. Following the addition of the adhesive, hollow cylindrical cover 218, is disposed about the cylindrical sleeve 190, securing the sleeve 190 in a proximal annular interference-fitting region 220 and a distal annular interference-fitting region 222. Note that while the cylindrical cover 218 is interference fit about the cylindrical sleeve 190 and insert 212, the fit is not tight enough to interfere significantly with the interior lumen.

Thus, annular raceways are created within the first hub 200, including a proximal reservoir 224 proximal to the proximal interference-fitting region 220, a distal reservoir 226 distal to the distal interference-fitting region 222 and an inner reservoir 228 in fluid communication with first hub lumen 202 and bordered by both interference-fitting regions. The proximal and distal reservoirs are designed as reservoirs for the retention of adhesive, while the inner reservoir is designed to bathe the ports 230 (shown in FIGS. 20 and 22) in the longitudinal bores 196 through which fluid medicament contained within the inner reservoir 228 may flow into the bores 196. Fluid within the bores 196, such as blood from delivery holes 208, 210 may also exit through the ports 230.

The use of ultraviolet-curable adhesives 214 in the present technology is a significant advance in the art because of the ports 230. If insert molding were employed to create a fluid tight seal, a manufacturer would be required to protect each of the ports 230 from melting and distortion during the hot insert molding process.

In order to create the desired reservoirs and interference-fitting regions, a variety of configurations are available. By way of example, and referring again to FIGS. 20 and 22, the cylindrical insert 212 preferably includes an annular ridge 232 having a wider diameter than the distal cylindrical portion 234 of the insert 212. These two insert surfaces, after being covered by the sleeve, mate at least partially with annular tiers within the hollow cylindrical cover 218.

As shown in FIG. 22, the preferred hollow cylindrical cover 218 comprises a first internal annular tier 236, a second internal annular tier 238, a third internal annular tier 240, a fourth internal annular tier 242, and a fifth internal annular tier 244, each of which increase in diameter as shown from the first tier to the fifth tier respectively. Thus, the proximal reservoir 224 is defined by the cylindrical sleeve 190, an annular ridge 232 of the insert 212, the fourth and fifth tiers, 242 and 244, and by an outer annular channel 246 existing in the shoulder 248 of the insert 212, and by a portion of the insert shoulder 248.

The inner reservoir 228 is defined by the proximal and distal interference fitting regions, 220, 222 the cylindrical sleeve 190, the third tier 240 and tube 204, bathing the cylindrical sleeve 190 such that the fluid enters the ports 230 shown in FIG. 20. Returning to FIG. 22, the distal reservoir 226 is defined by the first tier 236, a portion of the second tier 238, the distal interference fitting region 222, and the cylindrical sleeve 190. As shown in FIG. 21, an opening 250 between the sleeve 190 and the distal portion of the cylindrical cover 218 allows adhesive 214 to be wicked into the distal reservoir 226.

Adhesive 214 is disposed in the region surrounding the disposed proximal tip 216 in an amount sufficient to fill the proximal reservoir 224. As the cylindrical cover 218 is disposed about the cylindrical sleeve 190 and cylindrical insert 212, adhesive 214 is forced into and wicks into the proximal reservoir 224. The adhesive 214 may be disposed using an insertion device, such as a syringe filled with adhesive, and extension tube or another device known in the art for the placement of light-curable adhesive.

After the disposition of the cylindrical cover 218, adhesive 214 is placed within the distal opening 250, and wicks into the distal reservoir 226 attaching the sleeve 190 to the cover 218 such that the sleeve 190 does not balloon inward during use. The process of wicking occurs through capillary action of the uncured adhesive. Ultraviolet light such as from an ultraviolet light lamp 251 is then used to cure the adhesive 214 in the reservoirs through the translucent or transparent first hub 200. The entire first hub 200 may be subjected to a source of radiation such that the individual components are simultaneously bonded into a single cooperating unit. Preferably, however, the steps of placing adhesive in the annular tube reservoir 254 for connecting the anesthesia tube 204 to the first hub 200 and curing the adhesive are performed after the curing of the adhesive in the proximal and distal reservoirs.

In preferred embodiment of sleeve 190, the proximal portion 252 of the sleeve is flared as shown in FIG. 20 such that the proximal portion 252 can be more readily disposed about the distal insert portion 234 and the annular ridge 232. To maintain a tight fit, before disposing the sleeve 190 on the insert 212, the sleeve 190 may taper initially in region 253, then have a constant diameter on the inside sleeve surface (or widen only slightly in the proximal direction on the inside surface). Thus, upon disposition on the insert, 212 a tight fit may be achieved between the sleeve 190 and the distal insert portion 234 and an even tighter fit may be maintained on the wider annular ridge 232, such that the sleeve 190 more readily resists being removed from the insert 212. A part of the outer surface of the proximal portion 252, which stretches to fit over the annular ridge 232, may include a thickened region 255 which tapers at proximal end 194.

With continued reference to FIG. 20, a line 256 may be printed or otherwise marked to demonstrate the location of the delivery holes for the practitioner. Since the delivery holes 208, 210 are almost unobservable, the line 256 assists the practitioner in assuring that the delivery holes 208, 210 are properly located in the subcutaneous tissue.

As shown, in the embodiment of FIG. 19, the indwelling catheter apparatus may further include a second hub means as for example second hub 262, for providing fluid communication to the cannula 14. Hub 262 is joined in a fluid tight manner to proximal hub end 26 of cannula 14. As is also shown, second hub 262 can be connected to external tube 263, through which fluids may be infused to cannula 14. However, one skilled in the art will recognize that the second suture attachment ring 264 is optional, particularly in light of the neighboring first suture attachment ring 266 on first hub 200. Furthermore, it will be appreciated that it is possible to combine first hub 200 and second hub 262 such that an integrated light permeable hub assembly exists.

Figure 23:
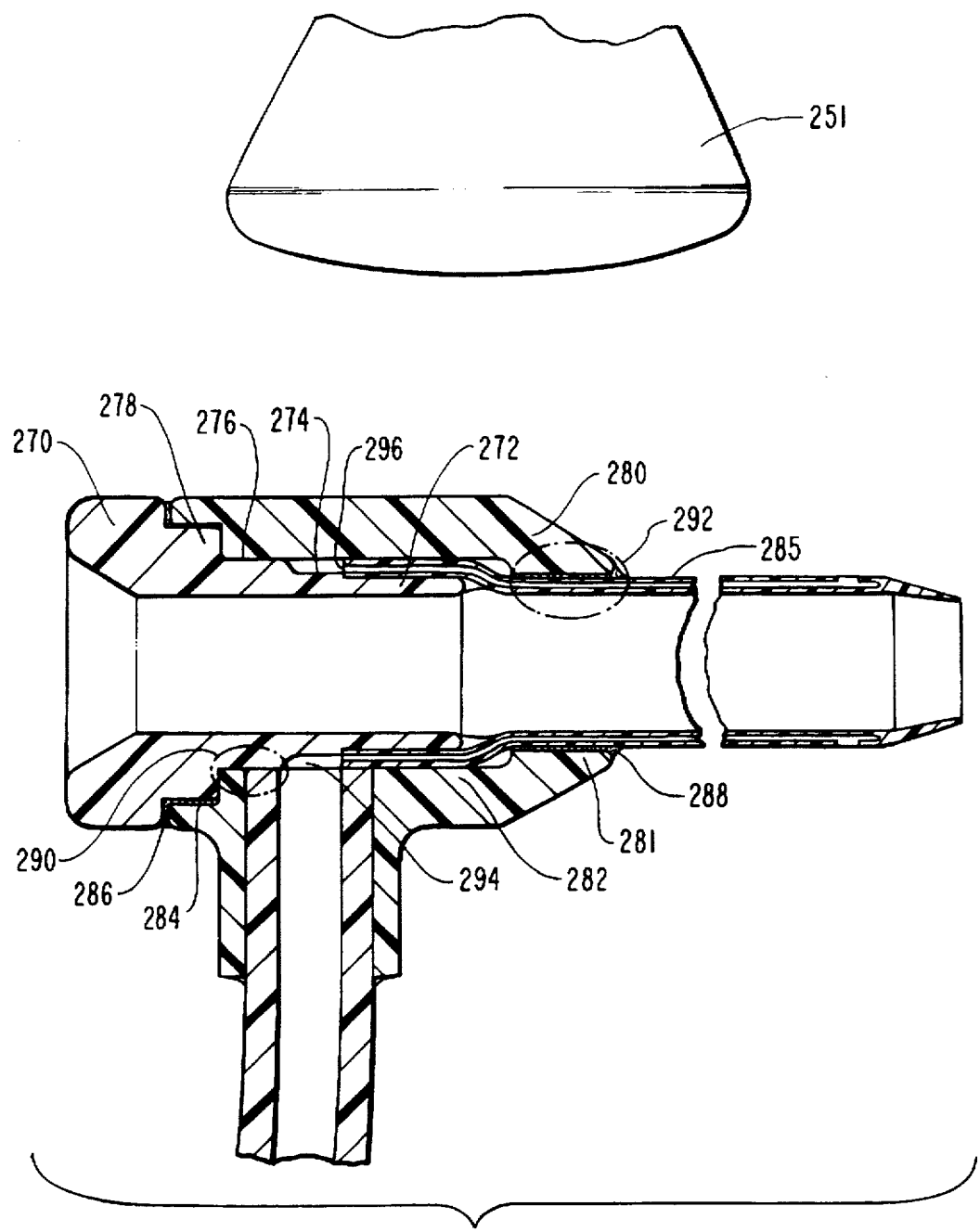
FIG. 23 is an alternate embodiment of the assembled hub illustrated in FIG. 22.

In another embodiment of the first hub 200A, shown in FIG. 23, the cylindrical insert 270 is comprised of a distal cylindrical portion 272, a first annular ridge 274, a second annular ridge 276, and a third annular ridge 278. The cylindrical cover 280 is comprised of a first annular tier 281, a second annular tier 282, and a third annular tier 284. A sleeve 285 is disposed over the cylindrical insert 270, after which a cylindrical cover 280 is disposed about the insert 270, creating a proximal reservoir 286, a distal reservoir 288 and proximal and distal interference fitting regions 290 and 292. An inner reservoir 294 is located between the interference fitting regions. In this embodiment, however, the proximal tip 296 of the sleeve is not sealed, but instead, provides entrance holes for fluid medicament. Thus, it is possible for the proximal tip 296 to serve as the entrance region for the interior lumen.

Ultraviolet curable adhesives are made of high boiling acrylate monomers and aliphatic-urethane acrylate oligomers with photo initiators, which comprise one component adhesives that cure rapidly when exposed to ultraviolet radiation and/or visible radiation of sufficient intensity to form flexible transparent bonds. Such adhesives are produced, for example, by Loc-Tite Corporation or Dymax Corporation.

The present invention may be embodied in other specific forms without departing from its spirit or essential characteristics. The described embodiments are to be considered in all respects in all respects only as illustrated and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An indwelling catheter apparatus comprising:

catheter means for insertion through subcutaneous tissue, said catheter means comprising an indwelling cannula adapted for insertion through subcutaneous tissue into a patient's body, and having an indwelling distal end and a proximal hub end adapted for securement outside of the body;

sheath means disposed about a portion of the canula for delivering fluid medicament to essentially only the subcutaneous tissue surrounding said cannula, said sheath means including a plurality of delivery holes, each of said delivery holes providing a fluid communication path between the sheath means and the surrounding subcutaneous tissue for said fluid medicament; and light permeable hub means for delivering fluid medicament to the sheath means, the light permeable hub means joined with ultraviolet activated adhesive in a fluid-tight manner to a proximal portion of the sheath means such that the sheath means is retained in a predetermined position with respect to the hub means.

2. An indwelling catheter apparatus as in claim 1, wherein the hub means is transparent.

3. An indwelling catheter apparatus as in claim 1, wherein the hub means is translucent.

4. An indwelling catheter apparatus as in claim 1, wherein the proximal portion of the sheath means is disposed about a proximal hub component and surrounded by a distal hub component.

5. An indwelling catheter apparatus as in claim 4, wherein the proximal portion of the sheath means is interposed between the proximal and distal hub components in a first region and in a second region.

6. An indwelling catheter apparatus as in claim 1, wherein the hub means further comprises:

a proximal adhesive reservoir;

a distal adhesive reservoir; and a cavity for receiving fluid medicament.

7. An indwelling catheter apparatus as in claim 6, wherein the sheath means is oriented such that ports in the sheath means are located within the cavity, allowing fluid medicament to flow between the cavity and the sheath means.

8. An indwelling catheter apparatus comprising:

catheter means for insertion through subcutaneous tissue, said catheter means comprising an indwelling cannula adapted for insertion through subcutaneous tissue into a patient's body, and having an indwelling distal end and a proximal hub end adapted for securement outside of the body;

sheath means disposed about a portion of the cannula, the sheath means comprising a plurality of longitudinal bores for delivering fluid medicament to essentially only the subcutaneous tissue surrounding the cannula;

a plurality of valve means for communicating the fluid medicament from the plurality of longitudinal bores to the subcutaneous tissue surrounding the sheath means; and light permeable hub means for delivering fluid medicament to the sheath means, the light permeable hub means joined with ultraviolet activated adhesive in a fluid-tight manner to a proximal portion of the sheath means such that the sheath means is retained in a predetermined position with respect to the hub means.

9. An indwelling catheter apparatus as in claim 8, wherein the sheath means is selectively removable from the catheter means.

10. An indwelling catheter apparatus as in claim 8, wherein the sheath means further comprises means for sealing the sheath means in a fluid tight manner about the cannula so as to prevent fluids from escaping between the cannula and the sheath means.

11. An indwelling catheter apparatus as in claim 8, wherein each valve means comprises a hole which allows the free flow of fluid into and out of each longitudinal bore such that the location of the sheath means can be regulated.

12. An indwelling catheter apparatus as in claim 8, wherein the longitudinal bores are uniformly spaced within the sheath means and are substantially parallel to a primary lumen running through the cannula.

13. An indwelling catheter apparatus as in claim 8, wherein a proximal portion of the sheath means is disposed about a proximal hub component and surrounded by a distal hub component.

14. An indwelling catheter apparatus as in claim 13, wherein the proximal portion of the sheath means is interposed between the proximal and distal hub components in a first region and in a second region.

15. An indwelling catheter apparatus as in claim 8, wherein the hub means further comprises:
a proximal adhesive reservoir;
a distal adhesive reservoir; and
a cavity for receiving fluid medicament located between the first and second reservoirs.

16. An indwelling catheter apparatus as in claim 15, wherein the sheath means is oriented such that a port in each longitudinal bore is located within the cavity, allowing fluid medicament to flow between the cavity and the longitudinal bore.

17. An indwelling catheter apparatus comprising:
catheter means for insertion through subcutaneous tissue, said catheter means comprising an indwelling cannula adapted for insertion through subcutaneous tissue into a patient's body, and having an indwelling distal end and a proximal hub end adapted for securement outside of the body;

sheath means selectively disposed about a portion of the cannula, the sheath means comprising a plurality of longitudinal bores for delivering fluid medicament to essentially only the subcutaneous tissue surrounding the cannula;

each longitudinal bore having a hole which allows the free flow of fluid medicament into and out of each longitudinal bore such that the location of the sheath means can be regulated; and light permeable hub means for delivering fluid medicament to the plurality of longitudinal bores, the light permeable hub means joined with ultraviolet activated adhesive in a fluid-tight manner to the proximal end of the sheath means such that the sheath means is retained in a predetermined position with respect to the hub means, the light permeable hub means comprising a proximal hub component and a distal hub component wherein a proximal portion of the sheath means is disposed about a proximal hub component and surrounded by a distal hub component.

18. An indwelling catheter apparatus as in claim 17, wherein the sheath means further comprises means for sealing the sheath means in a fluid tight manner about the cannula so as to prevent fluids from escaping between the cannula and the sheath means.

19. An indwelling catheter apparatus as in claim 17, wherein the longitudinal bores are uniformly spaced within the sheath means and are substantially parallel to a primary lumen running through the cannula.

20. An indwelling catheter apparatus as in claim 17, wherein the proximal portion of the sheath means is interposed between the proximal and distal hub components in a first region and in a second region; and wherein the hub means further comprises:
a proximal adhesive reservoir proximal to the first region;
a distal adhesive reservoir distal to the second region; and
a cavity located between the first and second regions for receiving fluid medicament.

21. An indwelling catheter apparatus as in claim 20, wherein the sheath means is oriented such that a port in each longitudinal bore is located within the cavity, allowing fluid medicament to flow between the cavity and the longitudinal bore.

* * * * *

UNITED STATES PATENT AND TRADEMARK OFFICE
CERTIFICATE OF CORRECTION

PATENT NO. : 5,797,886

DATED : Aug. 25, 1998

INVENTOR(S) : Robert Roth; Fred P. Lampropoulos; Jim Mottola; Arlin Dale Nelson; Jerrold L. Foote It is certified that error appears in the above-identified patent and that said Letters Patent are hereby corrected as shown below:

Col. 8, line 31, after "fluid" change "medicant" to --medicament--

Col. 8, line 48, after "Teflon" change "ployurethane" to --polyurethane--

Signed and Sealed this

Eighth Day of February, 2000

Attest:

Q. TODD DICKINSON

Attesting Officer

Commissioner of Patents and Trademarks